(12) United States Patent
Garner et al.

(10) Patent No.: US 10,066,193 B2
(45) Date of Patent: Sep. 4, 2018

(54) TARGETED PERFORMANCE OF HYPOHALITE METHODS THEREOF

(71) Applicant: THE CLOROX COMPANY, Oakland, CA (US)

(72) Inventors: Dewain Garner, Copley, OH (US); William L. Smith, Pleasanton, CA (US); Jared Heymann, Pleasanton, CA (US)

(73) Assignee: The Clorox Company, Oakland, CA (US)

(*) Notice: Subject to any disclaimer, the term of this patent is extended or adjusted under 35 U.S.C. 154(b) by 176 days.

(21) Appl. No.: 15/285,314

(22) Filed: Oct. 4, 2016

(65) Prior Publication Data
US 2017/0022453 A1 Jan. 26, 2017

Related U.S. Application Data

(63) Continuation of application No. 14/671,144, filed on Mar. 27, 2015, now Pat. No. 9,499,774, which is a
(Continued)

(51) Int. Cl.
*C11D 3/10* (2006.01)
*C11D 3/16* (2006.01)
(Continued)

(52) U.S. Cl.
CPC ........... *C11D 3/3951* (2013.01); *A01N 47/44* (2013.01); *A01N 59/00* (2013.01); *B05C 9/06* (2013.01);
(Continued)

(58) Field of Classification Search
CPC ... C11D 3/3951; C11D 3/3953; C11D 3/3955; C11D 3/3956; C11D 3/3958; C11D 11/0017; C11D 11/0023; C11D 17/041
(Continued)

(56) References Cited

U.S. PATENT DOCUMENTS 2,535,972 A * 12/1950 Vitalis ............... C11D 1/22
510/357
3,706,670 A 12/1972 Gray
(Continued)

FOREIGN PATENT DOCUMENTS

CA 1087955 A1 10/1980
EP 1130083 A1 3/2000
(Continued)

OTHER PUBLICATIONS

Lister, M.W., et al., "The Oxidation of Nitrite and Iodate Ions by Hypochlorite ions", Can. J. Chem., vol. 39, pp. 1645-1651 (1961).
(Continued)

*Primary Examiner* — Gregory R Delcotto
(74) *Attorney, Agent, or Firm* — Alok Goel

(57) ABSTRACT

This invention relates to extend the benefits of using hypochlorite compounds such as sodium hypochlorite to clean and disinfect articles while reducing or eliminating the side effects of treating an article with a strong oxidant material. The invention relates to a single step process involving mixing of precursor compositions of a suitable hypohalite or hypohalous acid with a solution of a reducing agent. Optionally a buffer may be present in either or both precursor compositions, such that at time of use such active hypohalous acid concentration in the resulting aqueous mixture remains at a sufficient activity level to effect one or more desired benefits against a target substrate for a desired period of time. The oxidant is substantially consumed by reaction with the reducing agent after the time needed for achieving the desired benefit has passed.

17 Claims, 14 Drawing Sheets

Related U.S. Application Data continuation of application No. 13/672,911, filed on Nov. 9, 2012, now Pat. No. 9,029,311.

(60) Provisional application No. 61/600,348, filed on Feb. 17, 2012.

(51) Int. Cl.

| | | |
|---|---|---|
| *C11D 3/26* | (2006.01) | |
| *C11D 3/395* | (2006.01) | |
| *A01N 59/00* | (2006.01) | |
| *C11D 7/10* | (2006.01) | |
| *B65D 25/04* | (2006.01) | |
| *B65D 25/08* | (2006.01) | |
| *B65D 85/00* | (2006.01) | |
| *B05C 9/06* | (2006.01) | |
| *C11D 3/00* | (2006.01) | |
| *C11D 3/04* | (2006.01) | |
| *C11D 17/04* | (2006.01) | |
| *A01N 47/44* | (2006.01) | |
| *C11D 3/22* | (2006.01) | |

(52) U.S. Cl.
CPC ............ *B65D 25/04* (2013.01); *B65D 25/08* (2013.01); *B65D 85/70* (2013.01); *C11D 3/0042* (2013.01); *C11D 3/0047* (2013.01); *C11D 3/048* (2013.01); *C11D 3/10* (2013.01); *C11D 3/26* (2013.01); *C11D 3/3953* (2013.01); *C11D 3/3955* (2013.01); *C11D 3/3956* (2013.01); *C11D 3/3958* (2013.01); *C11D 7/10* (2013.01); *C11D 7/105* (2013.01); *C11D 17/041* (2013.01); *C11D 3/22* (2013.01)

(58) Field of Classification Search
USPC ....... 510/238, 303, 379, 380, 381, 435, 439, 510/509; 8/137; 134/42; 252/187.25, 252/187.26
See application file for complete search history.

(56) References Cited

U.S. PATENT DOCUMENTS

| | | | |
|---|---|---|---|
| 3,717,580 | A | 2/1973 | Echols et al. |
| 3,749,672 | A | 7/1973 | Rutkiewic et al. |
| 4,167,561 | A | 9/1979 | Lamberti et al. |
| 4,236,891 | A | 12/1980 | Scardera et al. |
| 4,295,985 | A | 10/1981 | Petrow et al. |
| 4,552,679 | A | 11/1985 | Schobel et al. |
| 4,671,972 | A | 6/1987 | Schobel et al. |
| 4,980,215 | A | 3/1990 | Perlman |
| 5,403,402 | A | 4/1995 | LeGrow |
| 5,462,713 | A | 10/1995 | Schlitzer et al. |
| 6,663,306 | B2 | 12/2003 | Policicchio et al. |
| 6,718,992 | B1 | 4/2004 | Cardola |
| 7,357,248 | B2 | 4/2008 | Sivakumar et al. |
| 7,448,556 | B2 | 11/2008 | Muehlhausen et al. |
| 7,517,568 | B2 | 4/2009 | Bitowft et al. |
| 7,521,409 | B2 | 4/2009 | Tuggle |
| 7,527,783 | B2 | 5/2009 | Shaheen et al. |
| 7,629,305 | B1 | 12/2009 | Szekeres |
| 7,718,122 | B2 | 5/2010 | Smith et al. |
| 7,758,807 | B2 | 7/2010 | Smith et al. |
| 8,007,819 | B2 | 8/2011 | Shaheen et al. |
| 8,008,238 | B2 | 8/2011 | Malet et al. |
| 2002/0039988 | A1 | 4/2002 | Kasturi |
| 2002/0166779 | A1 | 11/2002 | Etesse et al. |
| 2003/0073604 | A1* | 4/2003 | McGoff ................ C11D 3/222 510/441 |
| 2005/0216291 | A1 | 9/2005 | Shaheen et al. |
| 2005/0221113 | A1 | 10/2005 | Bitowft et al. |
| 2005/0232847 | A1 | 10/2005 | Bromberg et al. |
| 2005/0232848 | A1 | 10/2005 | Nguyen et al. |
| 2005/0233900 | A1 | 10/2005 | Smith et al. |
| 2006/0100121 | A1 | 5/2006 | Tuggle |
| 2006/0102656 | A1 | 5/2006 | Troost et al. |
| 2006/0177521 | A1 | 8/2006 | Bromberg et al. |
| 2007/0029344 | A1 | 2/2007 | Schymitzek et al. |
| 2007/0111917 | A1 | 5/2007 | Lang et al. |
| 2007/0167340 | A1 | 7/2007 | Barthel et al. |
| 2007/0231247 | A1 | 10/2007 | Bromberg et al. |
| 2007/0253926 | A1 | 11/2007 | Tadrowski et al. |
| 2008/0003171 | A1 | 1/2008 | Smith et al. |
| 2009/0004234 | A1 | 1/2009 | Kessler et al. |
| 2009/0054295 | A1 | 2/2009 | Vicari et al. |
| 2009/0148342 | A1 | 6/2009 | Bromberg et al. |
| 2009/0165228 | A1 | 7/2009 | Kilkenny |
| 2009/0325842 | A1 | 12/2009 | DeDominicias |
| 2010/0009889 | A1 | 1/2010 | Smith et al. |
| 2010/0056415 | A1 | 3/2010 | Rong et al. |
| 2010/0255121 | A1 | 10/2010 | Perry |
| 2011/0262318 | A1 | 10/2011 | Hofte et al. |
| 2012/0237616 | A1 | 9/2012 | Panicheva et al. |

FOREIGN PATENT DOCUMENTS

| | | |
|---|---|---|
| GB | 2437489 A | 10/2007 |
| JP | 2004002229 | 1/2004 |
| WO | 9111751 A1 | 8/1991 |
| WO | WO9905310 | 2/1999 |
| WO | 200061712 A1 | 10/2000 |
| WO | 200061713 A1 | 10/2000 |
| WO | 200418319 A1 | 3/2004 |
| WO | 200549779 A1 | 6/2005 |
| WO | 2005094438 A2 | 10/2005 |
| WO | 2005094439 A2 | 10/2005 |
| WO | 200652638 A2 | 5/2006 |
| WO | 2010132948 A1 | 11/2010 |
| WO | 2011025949 A1 | 3/2011 |

OTHER PUBLICATIONS

"Kinetics and mechanism of nitrite oxidation by hypochlorous acid in the aqueous phase"; Nazafarin Lahoutifard et al.; 2003 Elsevier Science Ltd; Chemosphere 50 (2003) pp. 1349-1357.

PCT International Search Report PCT/US2012/64678; dated Jan. 22, 2013.

U.S. Office Action dated May 10, 2013 in U.S. Appl. No. 13/672,461, filed Nov. 8, 2012.

U.S. Office Action dated Feb. 28, 2014 in U.S. Appl. No. 13/672,461, filed Nov. 8, 2012.

U.S. Office Action dated Aug. 27, 2014 in U.S. Appl. No. 13/672,911, filed Nov. 9, 2012.

U.S. Office Action dated Dec. 11, 2014 in U.S. Appl. No. 13/672,461, filed Nov. 8, 2012.

U.S. Office Action dated Dec. 26, 2014 in U.S. Appl. No. 13/672,955, filed Nov. 9, 2012.

U.S. Office Action dated Aug. 1, 2016 in U.S. Appl. No. 14/671,144, filed Mar. 27, 2015.

* cited by examiner

TARGETED PERFORMANCE OF HYPOHALITE METHODS THEREOF

CROSS REFERENCE TO RELATED APPLICATIONS

This application is a continuation of U.S. patent application Ser. No. 14/671,144, filed on Mar. 27, 2015, now U.S. Pat. No. 9,499,774, which is continuation of U.S. patent application Ser. No. 13/672,911, filed Nov. 9, 2012, and now U.S. Pat. No. 9,029,311, which claims the benefit of U.S. Provisional Patent Application No. 61/600,348, filed Feb. 17, 2012 entitled TARGETED PERFORMANCE OF HYPOHALITE COMPOSITIONS, METHODS AND SYSTEMS THEREOF, the disclosures of which are incorporated herein in their entirety.

BACKGROUND OF THE INVENTION

1. The Field of the Invention

The present invention relates to hypohalite-based cleaners for use on hard, soft, animal and human surfaces.

2. Description of Related Art

Currently, hypohalite based cleaners achieve great efficacy for cleaning, bleaching, and disinfection. However, these cleaners have some negative side effects. Hypohalite based cleaners typically contain strong bleaching species and have certain undesirable side effects associated with their use such as strong odors, tendency to overbleach, surface corrosion, and a tendency to leave behind chlorinated species, such as chloramines, which leave an unpleasant odor after treatment. Thus, there is a continuing need for a cleaner that could leverage the benefits of hypochlorite bleach usage while minimizing or preventing any negative side effects. Surprisingly, the present invention addresses these issues.

BRIEF SUMMARY OF THE INVENTION

One aspect of the invention is directed to a method for preparing a mixed composition and treating a surface; the method comprising: providing a two-part composition comprising: an oxidant first part comprising a hypohalous acid or a hypohalite; and a reductant second part comprising a nitrite, wherein the first and second parts are initially separate from one another; mixing the oxidant first part with the reductant second part to form a mixed composition that provides oxidizing benefits for a limited duration, the oxidant reacting with a reductant to reduce the oxidant concentration so as to prevent or minimize negative side effects to the surface otherwise associated with prolonged oxidant exposure longer than the limited duration; and contacting the mixed composition with a surface to provide oxidizing benefits to the surface for a limited duration while preventing or minimizing negative side effects to the surface associated with prolonged oxidant exposure.

In another aspect of the invention, there is a method for preparing a mixed composition and treating a surface, the method comprising: providing a two-part composition comprising: an oxidant first part comprising a hypochlorite, the hypochlorite comprising up to about 15% by weight of the two-part composition; and a reductant second part comprising a nitrite, the nitrite comprising from about 0.01% to about 15% by weight of the two-part composition, wherein the first and second parts are initially separate from one another; mixing the oxidant first part with the reductant second part to form a mixed composition that provides oxidizing benefits for a limited duration, the oxidant reacting with a reductant to reduce the oxidant concentration so as to prevent or minimize negative side effects to the surface otherwise associated with prolonged oxidant exposure longer than the limited duration; and contacting the mixed composition with a surface to provide oxidizing benefits to the surface for a limited duration while preventing or minimizing negative side effects to the surface associated with prolonged oxidant exposure.

In yet another embodiment of the method, there is a method for preparing a mixed composition and treating a surface, the method comprising: providing a two-part composition comprising: an oxidant first part comprising a hypohalite, the hypohalite consisting of sodium hypohalite; and a reductant second part comprising a nitrite, the nitrite consisting of sodium nitrite, wherein the first and second parts are initially separate from one another; mixing the oxidant first part with the reductant second part to form a mixed composition that provides oxidizing benefits for a limited duration, the oxidant reacting with a reductant to reduce the oxidant concentration so as to prevent or minimize negative side effects to the surface otherwise associated with prolonged oxidant exposure longer than the limited duration; and contacting the mixed composition with a surface to provide oxidizing benefits to the surface for a limited duration while preventing or minimizing negative side effects to the surface associated with prolonged oxidant exposure.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof which are illustrated in the drawings located in the specification. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Definitions

Figure 1:
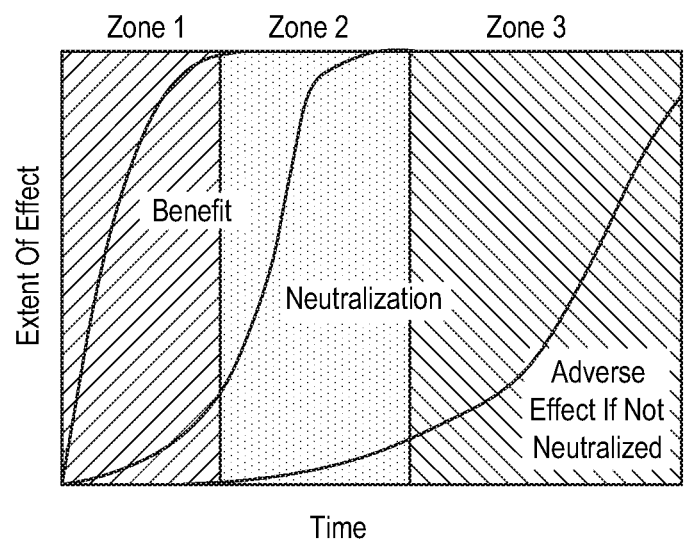
FIG. 1 is a plot showing conceptual zones related to the present invention including a beneficial zone, a quenching zone and a detrimental zone.

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising" which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more such surfactants.

As used herein, the term "disinfect" shall mean the elimination of many or all pathogenic microorganisms on surfaces with the exception of bacterial endospores.

As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant."

As used herein, the term "sterilize" shall mean the complete elimination or destruction of all forms of microbial life and which is authorized under the applicable regulatory laws to make legal claims as a "sterilant" or to have sterilizing properties or qualities.

The "reductant/oxidant Ratio" or "RIO" ratio is defined as a molar ratio, being the molar equivalents of reductant present divided by the molar equivalents of oxidant present in the combined compositions of the invention, thus being a ratio of the total reductant molar concentration to the total oxidant molar concentration present, and not a weight nor volume ratio of the materials. The RIO ratio may be denoted as a simple number or in ratio format with respect to 1, for example "5" or "5:1".

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage ("wt %'s") are in wt % (based on 100 weight % active) of the particular material present in the referenced composition, any remaining percentage being water or an aqueous carrier sufficient to account for 100% of the composition, unless otherwise noted. For very low weight percentages, the term "ppm" corresponding to parts per million on a weight/weight basis may be used, noting that 1.0 wt % corresponds to 10,000 ppm.

II. Introduction

This invention relates to compositions, methods and systems of providing the benefits of using hypochlorite compounds such as sodium hypochlorite to clean and disinfect articles while reducing or eliminating the side effects associated with treating an article with a strong oxidant material. The invention further relates to a single step process involving mixing a hypochlorite (e.g., sodium hypochlorite) with a reducing agent and optionally, a buffer at the time of use such that the hypochlorite ion or hypochlorous acid concentration in the resulting aqueous mixture remains at a sufficient activity level to effect one or more desired benefits against a target substrate for a desired period of time, while providing that the oxidant is then substantially consumed by reaction with the reducing agent after the time needed for achieving the desired benefit has passed. Desired benefits enabled by the present invention include, but are not limited, to the ability to effectively sterilize, disinfect and/or bleach the surface of an article, or an article itself, while extinguishing remaining oxidant to minimize and/or prevent further oxidation, surface corrosion, dye damage and the like.

This invention has the further benefits of preventing side effects or damage caused by prolonged exposure to hypochlorite, such as surface damage, dye discoloration or malodor generation, while providing benefits of hypochlorite use, including but not limited to disinfection, sterilization, stain removal, deodorization, mold removal, toxin and/or allergen remediation, and/or laundry textile bleaching and whitening. In one embodiment of the invention, the precursor compositions, mixed precursor compositions and associated methods of use herein provide a single step, convenient to use application of a "time of use" composition which does not require post mixing manipulation by the user. Another embodiment provides a shelf stable product including two precursor compositions that can be stored and mixed before or at time of use to provide an end use composition in which stability of a strong oxidant has been maximized for commercial and retail usage.

A need exists for compositions, systems and methods that can provide a one step aqueous composition formed by mixing a hypochlorite species with a reducing agent at the time of use that is capable of limiting in a predictable and controllable way the time that an article is exposed to the hypochlorite. To that end, it has surprisingly been discovered that control over hypochlorite lifetime is highly dependent on solution conditions such as the ratio of reductant to hypochlorite oxidant species and pH. It has also been discovered that many different reductants may be used and that these can be selected based on the operational conditions desired. This discovery led to the further discovery that hypochlorite lifetime may be adjusted as desired by the careful selection of operational conditions such as pH and R/O ratio and reductant identity.

It has been further discovered that a combination of one or more reducing agents may be used to control the lifetime of the hypochlorite component after mixing of the precursor compositions to form the usage composition. A further discovery is that addition of a buffer to such a time of use mixed system provides optimal performance in terms of the ability to "tune" the exposure time of the active bleaching system. Additionally, the present invention has the further advantage in that it may be used to deliver benefits derived from use of additional compounds and materials, such as surfactants, dyes and fragrances, which may be only marginally stable in the presence of hypochlorite over a typical product shelf life. Such optional components may be delivered simultaneously along with the primary bleaching and disinfectant benefit of the strong hypochlorite species where previously not achievable, e.g., because the two precursor compositions may be stored or maintained separately prior to the time of mixing.

One aspect of the invention relates to a single step process involving mixing an oxidant (e.g., sodium hypochlorite) with a reducing agent at the time of use such that the hypochlorite ion or hypochlorous acid concentration in the resulting aqueous mixture remains sufficient to effect the desired benefit for a desired period of time, while also providing that the oxidant is substantially consumed by reaction with the reducing agent after the time needed for achieving the desired benefit has passed. The composition may optionally include a buffer.

For example, one aspect of the invention is a single step process for activating and then timely deactivating a hypochlorite based oxidant, so as to achieve the desired benefits of performance on a treated article, while at the same time preventing side effects or damage caused by prolonged exposure to hypochlorite. Thus, the inventive embodiments provide one or more benefits of hypochlorite use, such as disinfection, sterilization, stain removal, deodorization, mold removal, toxin and/or allergen remediation, or laundry textile bleaching and whitening, while preventing negative side effects such as surface damage, dye discoloration and malodor generation.

One aspect of the invention relates to controlling the duration of zone 1 and zone 2. The duration of each zone depends on the desired benefit and the undesired effect to be avoided. Depending on the embodiment zone 1 may last for 30 seconds, 1 minute, 2 minutes, 5 minutes, 10 minutes, 30 minutes, 60 minutes, or any length of time encompassed within a range in which the end points of the range are defined by any of the above durations (e.g., 30 seconds to 60 minutes, 2 minute to 30 minutes, etc.). Depending on the embodiment zone 2 may last for 30 seconds, 1 minute, 2 minutes, 3 minutes, 5 minutes, 10 minutes, 20 minutes, 30 minutes, 60 minutes, or any length of time encompassed within a range in which the end points of the range are defined by any of the above durations.

FIG. 1 shows the zone of optimum utility (benefit) where achieving a maximal hypohalite bleach benefit with minimal adverse effects by neutralization of the hypohalite bleach after the desired benefit substantially occurs and before adverse effects substantially begin to affect the treated article. When thus viewed, treatment of a surface or article with an ideal improved hypohalite bleaching composition may be viewed as having three time zones of exposure. The first zone is the "benefit zone" and lasts long enough to substantially deliver the desired benefit to the treated surface or article. This benefit zone is generally shorter than the other two because of the rapid reactivity of hypohalite bleach species. In an ideal system, greater than about 50% of the initial hypohalite bleach concentration remains by the end of the benefit zone. Alternatively greater than about 60%, or greater than about 80% of the initial hypohalite bleach may remain.

The second zone is the "quenching zone" and is the time between substantial delivery of the benefit and detectable occurrence of the any detrimental aspects of treatment. Significant reduction of hypohalite bleach concentration ideally occurs during the duration of this quenching zone. Generally, the hypohalite concentration is reduced by at least 75% in this zone. Consequently, less than about 20% of the initial hypohalite bleach remains, alternatively less than about 10% of the initial hypohalite bleach, or alternatively less than about 5% of the initial hypohalite bleach remains by the end of this quenching zone. In some embodiments less than 1% of the initial hypohalite bleach remains at the end of this quenching zone.

The third zone is the "detrimental effect zone" and is denoted by the observance of some undesired effect of hypohalite bleach such as odor, dye damage or surface damage. This zone is usually longer than either of the previous zones. Its duration generally corresponds to a length of time it takes for any remaining hypohalite bleach to be consumed by reactions with soil, substrate or itself. In one embodiment, the hypohalite bleach concentration in zone 2 is sufficiently reduced to essentially prevent significant undesired effects that might otherwise occur in zone 3. In preferred embodiments of the invention, the quenching in zone 2 sufficiently reduces the concentration of hypohalite bleach such that zone 3 is essentially avoided. The quenching in zone 2 may sufficiently reduce the concentration of hypohalite bleach so that any undesired effects are acceptable, alternatively, any undesired effects in zone 3 are not objectionable. Still alternatively, the quenching is sufficient so that there are no detectable undesired effects.

III. Oxidant—Hypohalous Acid and Salts

In one embodiment of the invention, the compositions comprise hypohalite, defined as hypohalous acid and/or salts thereof. Suitable hypohalous acids and salts may be provided by a variety of sources, including compositions that lead to the formation of halide ions and/or hypohalite ions.

In another embodiment of the invention wherein the compositions herein are liquid, the hypohalite component may be an alkali metal and/or alkaline earth metal hypochlorite, or mixtures thereof. Compositions may include an alkali metal and/or alkaline earth metal hypochlorite selected from the group consisting of sodium hypochlorite, potassium hypochlorite, magnesium hypochlorite, lithium hypochlorite calcium hypochlorite, and mixtures thereof.

The hypohalous acid and/or salt composition may be an equilibrium mixture of hypochlorous acid and salts of hypochlorite. The active hypohalite specie(s) may be present in an amount from above zero to about 15 wt % of the composition, or from about 0.001 wt % (10 ppm) to about 10 wt % of the composition, or from about 0.005 (50 ppm) to about 5 wt % of the composition, or from about 0.005 wt % (50 ppm) to about 0.2 wt % (2000 ppm) of the composition.

In another embodiment a bromide salt may be added to convert all or part of the hypochlorite and/or hypochlorous acid to hypobromite and/or hypobromous acid. Examples of suitable bromide salts include, but are not limited to alkali metal salts of bromine, such as sodium bromide, potassium bromide, and combinations thereof. The bromide salt may be added in combination with the reductant. The inclusion of the bromide salt may advantageously alter the reaction rate with the reductant or enhance the benefit achieved from the hypohalous acids and salts. The bromide salt may be used in an amount sufficient to form hypobromite and/or hypobromous acid by conversion of about 0.001% to about 20%, or from about 0.01% to about 10%, or from about 0.1% to about 100%, or from about 1% to about 80%, or from about 25% to about 75%, or from about 80% to about 100% of the hypochlorite or hypochlorous acid.

The amount of available halogen oxidant in the composition may be determined by placing samples of the composition into about 50 milliliters of distilled water, followed by addition of about 10 milliliters of a 10 wt % solution of potassium iodide and addition of about 10 milliliters of a 10 volume % solution of sulfuric acid, the resulting mixture being well stirred. The resulting yellow to brown solution, whose color is the result of oxidation of free iodine ion (F) to molecular iodine ($I_2$), is then volumetrically titrated to an essentially colorless endpoint by addition of standardized 0.1 Molar sodium thiosulfate ($Na_2S_2O_3$) titrant. Calculation then expresses the result as percent of available molecular chlorine ($Cl_2$), that is to say assigning two equivalents per mole of titrated hypohalite oxidant. Stability results are then expressed by repeated assays over time using identically prepared samples resulting from the same composition, normalized to 100 percent representative of the starting available chlorine measured initially.

Alternatively, at lower concentrations of hypochlorite, generally below about 2,000 ppm or 0.2 wt %, spectroscopic measurement of the absorption of aqueous solutions may be used to monitor the concentration, and resulting changes, of the hypochlorous acid species in solution. The solution absorbs bluish light, accounting for the yellowish color of solutions including this oxidant. By use of controls, the relative level of hypochlorite can then be monitored and calculated by measuring absorbance of solutions by means of a suitable instrument, such as a spectrophotometer.

IV. Preferred Reductants

Generally, any compound capable of being solubilized into an aqueous solution that is capable of reacting with an oxidant such as hypochlorite ion or hypochlorous acid may be employed as a reductant in the present invention. Several exceptions are known and noted below as materials not suitable for use as reductants in the present invention.

A large number of materials are suitable as reductants, and may be selected for their particular properties and ability to control the beneficial exposure time of hypochlorous systems.

Reductants may be selected from several different groups, and selection of a reductant and/or group may be dependent on the desired operating conditions for the formula and its intended use. For example, physical characteristics of the potential reducing agent such as reduction potential, solubility, pKa, polarizability or dipole moment may be considered by one skilled in the art to assist in the selection of an appropriate reductant.

Reductants suitable for use in the present invention may in general be categorized in the following groups of materials sharing one or more similar chemical, physical, or reactive properties.

In one embodiment, reductants may be selected from Group 1 materials, which include, but are not limited to inorganic reducing agents such as the alkali or alkaline earth metal salts of nitrite, tetrathionate, and/or thiosulfate, similar materials, and combinations thereof. In one embodiment, the group 1 reductant comprises a nitrite.

In another embodiment, reductants may be selected from Group 2 materials, which include, but are not limited to, organo-nitrogen reducing agents such as guanidine hydrogen chloride, urea, amines, alkanolamines, alkylamides, alkanolamides, similar materials, and combinations thereof. Included in this group are polymers of organo-nitrogen reducing agents such as polyvinyl pyrrolidone and similar materials.

In another embodiment, reductants may be selected from Group 3 materials, which include, but are not limited to sugars, otherwise known in the art as monosaccharides, disaccharides and oligosaccharides. Included in this group are normal sugars, such as for example, the class of edible crystalline carbohydrates which include lactose and fructose. Also included in this group are reducing sugars, which are sugars having an open-chain form with an aldehyde group or a free hemiacetal group, including monosaccharides which contain an aldehyde group known as aldoses, and those with a ketone group known as ketoses. Also included in this group are polymeric sugars such as starches, carbohydrates, cellulose, gums, derivatives thereof, or like polymers which have at least one repeating monomer that is susceptible to oxidation as defined herein. Examples of suitable reducing sugars include, but are not limited to monosaccharides (e.g., glucose, glyceraldehyde and galactose); disaccharides, (e.g., lactose and maltose), similar materials, and combinations thereof.

In another embodiment, reductants may be selected from Group 4 materials, which include, but are not limited to chelating agents, sequestrants and similar materials capable of ionic binding with an alkaline earth metal counter cation (e.g., calcium or magnesium ions) such as disodium calcium EDTA (ethylene diamine tetra-acetic acid), BAPTA (1,2-bis (o-aminophenoxy)ethane-N,N,N',N'-tetraacetic acid), DTPA (Pentetic acid or diethylene triamine pentaacetic acid), EGTA (ethylene glycol tetraacetic acid), the like, and combinations thereof.

In another embodiment, reductants may be selected from Group 5 materials, which include, but are not limited to oxidizable organic acids and/or salts of organic acids which include the known organic carboxylic acids whose acidity is associated with having a carboxyl group (—COOH) such as sorbic acid or salts thereof, citric acid or salts thereof, lactic acid or salts thereof, ascorbic acid or salts thereof, maleic acid or salts thereof, fumaric acid or salts thereof, oxalic acid or salts thereof, acetic acid and salts thereof, glycolic acid and salts thereof, tartaric acid and salts thereof, and combinations thereof. Many other aliphatic and cycloaliphatic carboxylic acids and salts thereof with amino, hydroxyl, keto, sulfhydro or other oxidizable substituents, or that contain double or triple carbon-carbon bonds are also suitable. Also included in this group are polymers and copolymers of oxidizable organic acids which have at least one repeating monomer that is susceptible to oxidation as defined herein, such as polyacrylic acids and salts thereof, and combinations thereof.

In another embodiment, reductants may be selected from Group 6 materials, which include, but are not limited to alcohols such as methanol, ethanol, propanol, butanol, phenol, ethylene glycol and other similar materials and their isomers bearing at least one hydroxyl (—OH) group covalently bonded to an alkyl, aryl or phenyl group. Included in this group are polymeric alcohols which have at least one repeating monomer that is susceptible to oxidation as defined herein, such as polyvinyl alcohol and the like. Additional materials in this group include polyhydric alcohols, being those materials with more than one hydroxyl group, including but not limited to propylene glycol, glycerin, erythritol, xylitol, mannitol, sorbitol and similar materials, and combinations thereof.

In another embodiment, reductants may be selected from Group 7 materials, which include, but are not limited to oxidizable surfactants, which include those surfactants having a nitrogen or quaternary nitrogen functionality, such as lauryl amine oxide, benzalkonium chloride, lauryl dimethyl ammonium chloride, similar materials, and combinations thereof.

In another embodiment, more than one reductant may be selected. When employing multiple reductants, more than one reductant may be selected from a group or reductants from different groups may be combined.

Reductants may suitably be employed in the present invention at levels between about 0.01 wt % to about 15 wt %, or alternatively from about 0.05 wt % to about 10 wt %, or yet alternatively from about 0.1 wt % to about 1 wt %. Reductant molar ratios with respect to the oxidant (e.g., sodium hypochlorite) may be selected from a range from between about 0.01:1 to about 100:1, or alternatively from about 0.05:1 to about 50:1, or yet alternatively from about 0.1:1 to about 10:1.

Additionally, in further embodiments of the invention, low levels of halide salts such as sodium bromide and/or salts of bromine, iodine and/or salts of iodine, may be added to any of the above reductants (quenchers) to modify the reaction time with the hypochlorite or other hypohalide. Suitable levels of these halides and/or halide salts range from 0.0001 wt % to about 1 wt %, or alternatively from about 0.001 wt % to about 0.5 wt %, or yet alternatively from about 0.01 wt % to about 0.1 wt %. Reductant molar ratios with respect to the oxidant (e.g. sodium hypochlorite) may be selected from a range from between about 0.01:1 to about 100:1, or alternatively from about 0.05:1 to about 50:1, or yet alternatively from about 0.1:1 to about 10:1.

V. Examples of Unsuitable Reductants

Some materials that have been found to not work effectively as reductants in the present invention, either by reacting too quickly or too slowly to be of practical utility, include non-reducing sugars such as sucrose, hydrogen peroxide, sodium sulfite, non-oxidizable buffers such as the acids and salts of phosphates, borates, carbonates and the like; non-oxidizable salts such as sodium chloride, sodium sulfate, and the like; and saturated unbranched carboxylic acids without a double bond or an oxidizable substituent.

VI. Buffer

Suitable buffers include those materials capable of controlling ultimate solution pH and which themselves resist reaction with the oxidant and remain in sufficient concentration to control the pH throughout the entire duration of Zone 1 or the benefit period. Suitable buffers further include those buffers that are non-consumable with respect to action by the oxidant. In addition, other suitable buffers are selected from the group of those materials having an acid dissociation constant (Ka) at 20° C. in the range between $1 \times 10^{-2}$ and $1 \times 10^{-12}$, between $1 \times 10^{-3}$ and $1 \times 10^{-11}$, between $1 \times 10^{-3}$ and $1 \times 10^{-8}$, or between $1 \times 10^{-8}$ and $1 \times 10^{-12}$.

Buffers that can be used in the present inventive systems may be selected dependent on the desired pH of the final one step composition to be targeted. In some embodiments of the invention it may be desired to employ a combination of buffers of differing acid dissociation values to achieve optimal mixed solution conditions. In some embodiments of the invention, it is desirable to have the buffer concentration on a molar basis be less than the initial concentration of hypochlorite in order to adequately control the ultimate solution pH during the quenching reaction at a minimal cost. In additional embodiments of the invention, it is desirable to have a buffer concentration that is at least equally concentrated on a molar basis as the initial concentration of hypochlorite in order to adequately control the ultimate solution pH during the extent of the quenching reaction. In yet other embodiments of the invention, it is desirable to have a buffer concentration that is at least about twice as concentrated on a molar basis as the initial concentration of hypochlorite in order to adequately control the ultimate solution pH during the extent of the quenching reaction. In yet other embodiments of the invention, the buffer concentration may be greater than twice the initial molar concentration of hypochlorite for maximum control of the ultimate solution pH during the extent of the quenching reaction.

The following are non-limiting examples of buffers that may be used singly, or in combination to control the pH in embodiments of the inventive compositions. Suitable buffers include salts and/or corresponding conjugate acids and bases of the following classes of materials, and their derivatives: carbonates, bicarbonates, boric acid and borates, silicates, di- and mono-basic phosphates or phosphoric acid, mono-carboxylic or polycarboxylic acids such as acetic acid, succinic acid, octanoic acid, the like, and combinations thereof.

In addition, suitable buffers may include a combination of one or more buffering molecules and contain an additional inorganic acid (e.g., hydrochloric, phosphoric, sulfuric and/or nitric acid) or an organic acid (e.g., acetic acid) to adjust the buffer/quencher composition to the desired or appropriate solution pH to provide the ultimate desired pH when mixed with the hypohalous containing precursor composition to form the single step use compositions. Suitable buffers may include a combination of one or more buffering molecules and contain an additional inorganic base (e.g., sodium hydroxide and/or sodium silicate) in order to adjust the buffer/hypohalous precursor composition to the desired or appropriate solution pH to provide the ultimate desired pH when mixed with the buffered quencher precursor composition to form the single step use composition.

Appropriate ranges for the buffer in the present invention may be between about 0.01 wt % to about 15 wt %, or alternatively from about 0.05 wt % to about 10 wt %, or yet alternatively from about 0.1 wt % to about 1 wt %. The buffer molar ratio with respect to the hypohalite material present (i.e., buffer/oxidant molar ratios) may range from between about 0.01:1 to about 100:1, or alternatively from about 0.05:1 to about 50:1, or yet alternatively from about 0.1:1 to about 10:1.

One example embodiment of a buffer appropriate for a nitrite quencher at pH 8.5 as explored in the nitrite example section herein employs a 0.022 wt % sodium hypochlorite solution (oxidant composition), to be combined with 0.045 wt % sodium nitrite, 0.09 wt % sodium phosphate dibasic, and 0.06 wt % sodium carbonate with an additional 0.02 wt % hydrochloric acid on the quencher side (quencher composition) at the time of formulation to achieve a pH of about 8.26 in the quencher precursor composition. Upon mixing with the hypochlorite oxidant precursor composition at the time of use, the resulting pH of the ultimate inventive one step use composition is about 8.5, and the ultimate solution maintains this approximate pH throughout the reduction process during treatment of a target substrate.

Combinations of buffers may also occur upon mixing. For example, in one embodiment of the invention hypochlorite is buffered with carbonate before mixing and the reductant side is buffered with succinic acid before mixing. In another embodiment, a buffering system may include a mixed carbonate and succinic acid system.

Thus, additional embodiments are included in which compatible buffer materials may be added to the oxidant precursor composition and/or the reductant precursor compositions of the invention for convenience or other means.

VII. Other Optional Ingredients

Optional ingredients include, but are not limited to, surfactants, wetting agents, dispersing agents, hydrotropes, solvents, polymers, rheology control agents, chelating agents, abrasives, fragrances, colorants, anticorrosion agents and other functional additives.

The combined solution may contain an effective amount of a wetting agent to reduce the contact angle of the solution on the surface to about 30° or less. Alternatively, the contact angle may be about 20° or less, or about 10° or less. Ideally the contact angle will be as close as possible to 0° and the combined solution will readily flow into the cracks and crevasses of the surface to allow effective hypochlorite exposure. The wetting agent can be any substance commonly described in the art that does not react rapidly with hypochlorite anion or hypochlorous acid. These include surfactants, pairs of oppositely charged surfactants, polymeric wetting agents, and polyelectrolyte complexes of a charged polymer with an oppositely charged micelle of a single surfactant or a mixture of surfactants, and mixtures thereof.

Dispersing agents that enhance the removal of microorganisms from skin into suspension are also effective at increasing antimicrobial activity and sanitization. These may also be present in the combined solution. Total amounts of wetting agents and dispersing agents in the combined solution may typically be between about 5 mg/L to about 200 g/L, alternatively from about 10 mg/L to about 100 g/L, or from about 50 mg/L to about 50 g/L, or from about 100 mg/L to about 20 g/L. It is desirable to use the least amount of wetting and dispersing agents to provide effective wetting to minimize the amount of residue that may remain when the product is used without rinsing.

Exemplary wetting or dispersing agents include various surfactants (e.g., cationic surfactants, anionic surfactants, nonionic surfactants, amphoteric and/or zwitterionic surfactants), hydrotropes, polymers and copolymers. Cationic surfactants may also act as a phase transfer agent for the hypochlorous acid disinfecting agent. Mixtures of surfactants often produce better results than a single surfactant. Particularly effective are mixtures of cationic or pseudo-cationic surfactants with anionic surfactants that associate to synergistically decrease interfacial tensions and increase wetting and dispersion. Such mixtures are also more efficient so the required concentration is reduced while improving performance.

Particular exemplary cationic surfactants include alkyltrimethylammonium, alkylpryidinium, and alkylethylmorpholinium salts, in which the alkyl group contains 4 to 18 carbon atoms, alternatively 12 to 16 carbon atoms. The alkyl chains may be linear or branched or contain an aryl group. The counterion may be, but is not limited to, chloride, sulfate, methylsulfate, ethylsulfate, or toluene sulfonate. Other suitable cationic surfactants include dialkyldimethyl ammonium salts, in which the alkyl groups each contain 4 to 12 carbon atoms such as dioctyldimethyl ammonium chloride. Other suitable cationic surfactants may have two quaternary ammonium groups connected by a short alkyl chain such as N-alkylpentamethyl propane diammonium chloride. In the above cationic surfactants the methyl substituents can be completely or partially replaced by other alkyl or aryl substituents such as ethyl, propyl, butyl, benzyl, and ethylbenzyl groups, for example octyldimethylbenzyl ammonium chloride and tetrabutylammonium chloride.

Nitrogen containing surfactants may also act as phase transfer catalysts as well as wetting and dispersing agents. They may be amphoteric or zwitterionic. These include amine oxides, sarcosinates, taurates and betaines. Examples include $C_8$-$C_{18}$ alkyldimethyl amine oxides (e.g., octyldimethylamine oxide, lauryldimethylamine oxide, and cetyldimethylamine oxide), $C_4$-$C_{16}$ dialkylmethylamine oxides (e.g. didecylmethylamine oxide), $C_8$-$C_{18}$ alkyl morpholine oxide (e.g. laurylmorpholine oxide), tetra-alkyl diamine dioxides (e.g. tetramethyl hexanane diamine dioxide, lauryl trimethyl propane diamine dioxide), $C_8$-$C_{18}$ alkyl betaines (e.g. decylbetaine and cetylbetaine), $C_8$-$C_{18}$ acyl sarcosinates (e.g. sodium lauroylsarcosinate), $C_8$-$C_{18}$ acyl $C_1$-$C_6$ alkyl taurates (e.g. sodium cocoylmethyltaurate), $C_8$-$C_{18}$ alkyliminodipropionates (e.g. sodium lauryliminodipropionate), and combinations thereof.

Many other surfactants may also be suitable for use as dispersing agents within the hypochlorite disinfecting compositions of the present invention. Examples of anionic surfactants include, but are not limited to, $C_6$-$C_{16}$ fatty acid soaps (e.g. sodium laurate), $C_8$-$C_{18}$ linear or branched alkyl sulfates (e.g. sodium laurylsulfate, and sodium tetradecylsulfate), $C_6$-$C_{18}$ linear or branched alkyl sulfonates (e.g. sodium octane sulfonate and sodium secondary alkane sulfonate), alpha olefin sulfonates, $C_6$-$C_{16}$ acyl isethionates (e.g. sodium cocoyl isethionate), $C_6$-$C_{18}$ alkyl, aryl, or alkylaryl ether sulfates, $C_6$-$C_{18}$ alkyl, aryl, or alkylaryl ether methylsulfonates, $C_6$-$C_{18}$ alkyl, aryl, or alkylaryl ether carboxylates, sulfonated alkyldiphenyloxides (e.g. sodium dodecyldiphenyloxide disulfonate), and combinations thereof.

Examples of nonionic surfactants include, but are not limited to, mono or poly alkoxylated (e.g. ethoxylated or propoxylated) $C_6$-$C_{12}$ linear or branched alkyl phenols, $C_6$-$C_{22}$ linear or branched aliphatic primary or secondary alcohols, and $C_2$-$C_8$ linear or branched aliphatic glycols. Block or random copolymers of $C_2$-$C_6$ linear or branched alkylene oxides are also suitable nonionic surfactants. Capped nonionic surfactants in which the terminal hydroxyl group is replaced by halide; $C_1$-$C_8$ linear, branched or cyclic aliphatic ether; $C_1$-$C_8$ linear, branched or cyclic aliphatic ester; phenyl, benzyl or $C_1$-$C_4$ alkyl aryl ether; or phenyl, benzyl or $C_1$-$C_4$ alkyl aryl ester may also be used in this invention. Other suitable nonionic surfactants include mono or polyalkoxylated amides of the formula $R^1CONR^2R^3$ and amines of the formula $R^1NR^2R^3$ wherein $R^1$ is a $C_5$-$C_{31}$ linear or branched alkyl group and $R^2$ and $R^3$ are $C_1$-$C_4$ alkyl, $C_1$-$C_4$ hydroxyalkyl, or alkoxylated with 1-3 moles of linear or branched alkylene oxides.

Suitable alkylpolysaccharides for use herein are disclosed in U.S. Pat. No. 4,565,647 to Llenado, having a linear or branched alkyl, alkylphenyl, hydroxyalkyl, or hydroxyalkylphenyl group containing from 6 to 30 carbon atoms and a polysaccharide, e.g., a polyglycoside, hydrophilic group containing from 1.3 to 10 saccharide units. Suitable saccharides include, but are not limited to, glucosides, galactosides, lactosides, and fructosides. Alkylpolyglycosides may have the formula: $R^2O(CnH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 10.

Fatty acid saccharide esters and alkoxylated fatty acid saccharide esters are also suitable for use in the present invention. Examples include, but are not limited to, sucrose esters, such as sucrose cocoate, and sorbitan esters, such as polyoxyethylene(20) sorbitan monooleate and polyoxyethylene(20) sorbitan monolaurate.

A wide variety of phosphate ester surfactants are also suitable. These include mono, di, and tri esters of phosphoric acid with $C_4$-$C_{18}$ alkyl, aryl, alkylaryl, alkyl ether, aryl ether and alkylaryl ether alcohols (e.g. disodium octyl phosphate). Wetting and dispersing is also achieved using sulfonated short chain alkyl benzenes and naphthalenes (e.g. sodium xylene sulfonate and sodium methylnaphthalene sulfonate).

Wetting and dispersion may also be improved by including a hydrotrope. Examples of hydrotropes include, but are not limited to, water soluble salts of low molecular weight organic acids such as the alkali metal (sodium and/or potassium) salts of aromatic sulfonic acids, aliphatic sulfates, aliphatic sulfonates, and aliphatic carboxylates. Specific exemplary materials include, but are not limited to, toluene sulfonate, cumene sulfonate, xylene sulfonate, naphthalene sulfonate, methyl naphthalene sulfonate, octyl sulfate, octyl sulfonate, octanoic acid, decanoic acid, and combinations thereof.

The compositions can be further improved using relatively low molecular weight water soluble polymers. Such polymers aid dispersion, but usually do not decrease interfacial tensions as well as surfactants. These polymers may be anionic or cationic, or contain a mixture of cationic and anionic groups. Common polycarboxylate polymers are made from acrylic acid and maleic acid. These may also be copolymers with various olefins, methacrylate, styrene, methylvinylether, vinylpyrrolidone, etc. Polyvinylpyrrolidone is an example of a nonionic dispersant. Sulfonate groups can be included using sulfonated styrene or other sulfonated alkenes. Polysulfonated polymeric dispersants can also be made by sulfonating various alkyl or aryl polymers. Naphthalene sulfonate formaldehyde copolymers are also useful dispersants. Cationic groups can be included using alkenes with quaternary ammonium groups such as vinyl alkyl trimethylammonium, vinyl N-alkyl pyridinium, and vinyl N-alkylmorpholinium. An example of a cationic polymer is DADMAC, poly diallyl dimethyl ammonium chloride. Typically the water soluble polymer will have 10 to 1,000 monomer units, or 20 to 200 monomer units. Mixtures of polymers with oppositely charged surfactants may provide a synergistic decrease of interfacial tension, improved wetting, and improved dispersion.

The combined solution may contain an optional fragrance or perfume to impart a pleasant odor that masks the odor of hypochlorous acid and its reaction products with soils and proteins. Such fragrances may generally be mixtures of volatile and semi-volatile organic compounds that are readily available from commercial sources. Selected fragrances should comprise compounds that are slow to react with hypochlorous acid and be listed as inert materials by regulatory agencies such as the US FDA. Many suitable such compounds will be known to those of skill in the art in light of the present disclosure. The combined solution may have from about 1 mg/L to about 10 g/L of fragrance. The fragrance concentration may be from about 10 mg/L to about 5 g/L, alternatively from about 0.1 g/L to about 3 g/L, and yet, alternatively from about 0.1 g/L to about 2 g/L.

The combined solution may contain rheology control agents, thickeners, gelling agents and viscosity adjusters to provide the desired product feel and form. For example the combined solution could be a thickened liquid, a gel, or a foam. Suitable thickening agents include, for example, natural and synthetic gums or gum like materials such as gum tragacanth, carboxy-methylcellulose, polyvinyl pyrrolidone, and/or starch. Linear or branched polycarboxylate polymers are also suitable, especially various high molecular weight polycarboxylates with multiple chains that are linked together as substituents on a multi-functional molecule to create a star-like molecule. Inorganic thickeners including alumina, various clays, organo-modified clays, aluminates and silicates are also suitable thickening agents. Thickening can also be achieved using combinations of oppositely charged or pseudo-charged surfactants or combinations of surfactants and polymers. Examples include combinations of anionic surfactants such as fatty acids, alkyl sulfates, or alkyl sulfonates with cationic polymers such as DADMAC, polyallyldimethylammonium chloride, combinations of cationic or pseudo cationic surfactants such as alkyl pyridinium salts, alkyltrimethyl ammonium salts alkyldimethylamine oxides, alkyl betaines, or acylsarcosinates with anionic polymers, anionic surfactants, arylsulfonates, or substituted aryl sulfonates, and surfactants such as alkyl ether sulfates that thicken by balancing the alkyl chain length with the number of ether linkages. Various alkaline earth or alkali metal salts of phosphates, halides, carbonates, nitrates, borates, and sulfates can be used to adjust viscosity. The concentration of thickening agents in the combined solution may be from about 0.01 g/L to about 300 g/L, alternatively from about 1 g/L to about 100 g/L, and yet alternatively from about 5 g/L to about 50 g/L.

The combined solution may also contain surfactants as described above that create foam when the solution is dispensed. Certain combinations of surfactants will synergistically increase the amount and longevity of the foam. In addition other ingredients such as water soluble polymers and viscosity modifiers can increase the amount or longevity of the foam. The formulation can also include a foam booster to increase the amount or longevity of foam. Examples of foam boosters include, but are not limited to, fatty acid amides, alkoxylated fatty acid amides, fatty acid amides of alkanolamines, fatty acid amides of alkoxylated alkanolamines, and fatty acid amides of alkanolamide esters. Particles with diameters less than 1 micron can also be included to stabilize and enhance foams. Examples of such particles include, but are not limited to, precipitated soaps, precipitated or fumed silica, aluminosilicates, clays, zeolites, metal silicates, metal carbonates, metal oxides, metal hydroxides, and various nanoparticles of carbon or other elements.

The combined solution may contain a number of other adjuvants that provide functional benefits. These include, but are not limited to solvents, abrasives and surfactants for soil removal and cleaning; emulsifiers; rinse aids; drying agents; lubricants; and irritation reducers. Some functional adjuvants include inorganic salts, silicones, fats, fatty acids, fatty acid esters and ethers, squalene, lanolin and its derivatives, lecithin and its derivatives, polycarboxylic acid polymers and copolymers, hydrogenated poly aliphatic compounds, alkanes, parabens, alkyl parabens, gelatin, mica, talc, clay, titanium dioxide, pumice, UV absorbers, and similar compounds.

VIII. Uses

In one aspect of the invention, the products have target uses such as for the treatment of hard surfaces, soft surfaces, and air. In one embodiment, the inventive compositions have target uses that include treatment of human and animal surfaces.

Examples of hard surfaces to which the invention can be applied include surfaces composed of refractory materials such as: glazed and unglazed tile, porcelain, ceramics as well as stone including marble, granite, and other stones surfaces; glass; metals; plastics such as, but not limited to polycarbonate, styrene, polyester, vinyl; Fiberglass, FORMICA, CORIAN and other hard surfaces known in the industry. Other hard surfaces include lavatory fixtures such as shower stalls, bathtubs and bathing appliances (racks, shower doors, shower bars) toilets, bidets, wall and flooring surfaces.

Further hard surfaces include painted surfaces and those associated with kitchen environments and other environments associated with food preparation, including cabinets and countertop surfaces as well as walls and floor surfaces especially those which include refractory materials, plastics, FORMICA, CORIAN, and stone. Also included are joining materials commonly used in association with such surfaces, including but not limited to grout, caulking, rubber and vinyl sealant materials, gaskets, rubber and vinyl forms, stucco, mastic, plaster, concrete, mortar, silica, cement, polyurethane, and the like.

Examples of soft surfaces include clothing, fabrics, textiles, carpets, rugs, upholstery, and other textile covered furniture, curtains, draperies and the like made from natural and man-made fibers.

Further examples of soft surfaces include paper and pulp, and materials made from paper or cellulosic materials, including but not limited to wallpaper and fiberboard.

Examples of suitable human and animal surfaces that may be treated according to the present invention include skin, wounds, hair, teeth, fur and the mucous membranes.

In one embodiment, inventive compositions can be supplied directly to surfaces to effect treatment. In another embodiment, the inventive compositions can be diluted into water to treat submerged articles, such as for example, in laundry applications or bucket dilutions to clean shoes, toys and other small objects.

In another embodiment, the inventive compositions can be used as a disinfectant, sanitizer, and/or sterilizer to treat microbially challenged surfaces, articles and/or objects.

In yet another embodiment, the inventive compositions can be used to remove, denature or inactivate allergens or allergen generating species. Dust mites, house dust, animal dander, animal hair, and the like, represent a mix of substances that contain allergens. Not all substances found in dust mite, house dust, animal dander, animal hair, etc. are capable of inducing an immune response, much less an allergic response. Some of these substances are antigens and will induce a specific immune response. Some of these antigens are also allergens and will induce a hypersensitivity response in susceptible individuals. Common allergens present indoors include, but are not limited to, *Dermarophagoides pteronyssinus* and *Dermatophagoides farinae* (both from dust mites), *Felis domesticus* (from cats), *Canis familiaris* (from dogs), *Blatella germanica* (from German cockroach), *Penicillium, Aspergillus* and *Cladosporium* (from fungi), as well as allergens from outdoors that enter the indoor environment, e.g., pollen allergens.

In a further embodiment, the inventive compositions can be used on food preparation surfaces and can contain only food-safe ingredients. Compositions for use herein may contain only materials that are food grade or GRAS ("generally regarded as safe"), including, of course, direct food additives affirmed as GRAS, to protect against possible misuse by the consumer. Failure to rinse thoroughly after cleaning is less of a concern if all of the ingredients are GRAS and/or food grade. In the United States, the use and selection of cleaning ingredients for the purpose of washing fruits and vegetables is described by the United States Code of Federal Regulations, Title 21, Section 173. 315: "Ingredients for use in washing or to assist in the peeling of fruits and vegetables". These regulations restrict the ingredients that can be used for direct contact with food to those described as GRAS, and a few other selected ingredients. These sections also provide certain limitations on the amount of material that can be used in a given context.

In one embodiment, the present invention encompasses the method of spraying an effective amount of the composition for reducing malodor onto household surfaces. The household surfaces can be selected from the group consisting of countertops, cabinets, walls, floors, bathroom surfaces and kitchen surfaces. Other suitable household surfaces include pet areas, pet litter, litter boxes, pet bowls, and pets. The present invention encompasses the method of spraying a mist of an effective amount of the composition for reducing malodor onto fabric and/or fabric articles. The present invention relates to the method of spraying a mist of an effective amount of the composition into the air for reducing malodor impression to a consumer. The present invention relates to a method of spraying a mist of an effective amount of the composition onto cat litter, pet bedding and pet houses for reducing malodor impression or to consume malodor. The present invention also relates to methods of spraying a mist of an effective amount of the composition onto household pets for reducing malodor impression. In yet another embodiment, the inventive compositions may be used to treat mold, fungus, mildew, mildew spores, algae and surfaces and materials contaminated therewith, providing the benefit of bleaching, decolorization and removal of the contaminants, and further providing reduced odor from bleaching byproducts such as chloramines that would otherwise remain after treatment with hypohalite bleach alone.

In another embodiment, the invention encompasses compositions and methods for using them as wash additives for treating clothing and textiles for the purpose of disinfection, bleaching, whitening, and odor and stain removal. In other embodiments, the inventive compositions may be used to remove ink, wine, juice, food, clay and make-up stains from clothing and textiles, providing enhanced stain removal with reduced dye and fabric damage.

IX. Product Containers and Product Form

Any container adapted to separately hold and then deliver the two precursor compositions of the invention may suitably be employed. In the most basic embodiment the first precursor composition contains the oxidant and the second precursor composition contains a reductant and optionally a buffer. Alternatively, the first precursor composition contains the oxidant and an optional buffer and the second precursor composition contains a reductant. In alternative embodiments, either or both precursor compositions may contain additional surfactants, buffers, pigments, dyes, fragrances or other additives desired for product stability, appearance, performance or consumer acceptance.

In one embodiment, the hypochlorite composition is stored in one side of a dual container, while the reductant composition is stored on the other side of the container, and the two compositions are mixed by the action of opening both sides and pouring the two compositions into a third receptacle where they mix to form the inventive compositions described herein. The packaging may be sized so that a portion of each solution is dispensed for each use or premeasured into a unit dose so the entire contents are used for a single use. The components may be packaged in pouches, ampoules, bottles, water soluble films, or various other options. The components may be combined in various ratios depending on the composition of each component.

In other embodiments, dual pouches, segmented containers, sprayers which combine two liquid compositions during dispensing, one or more rollers which apply, individually or mixed, the liquid compositions to a surface, and/or two separate bottles or containers holding the two precursor compositions of the invention, may be employed. In a preferred embodiment, the two compartments will be combined into a single package that controls the mixing of the two components as the combined solution is dispensed.

In one aspect of the embodiment, the two chambers or compartments can be side by side and adjacent to each other in a substantially parallel arrangement. In an alternative aspect of the embodiment, one chamber is completely or partially contained within the other chamber. These two chambers may or may not be concentric. The chambers may have the same or different volumes depending on the concentrations of ingredients used in each component and the required mixing ratios. In one aspect of the embodiment, each chamber may have a connection to the delivery device. Examples of delivery devices include, but are not limited to, trigger sprayers, aerosol valves, flip-top dispensers, push-pull valves, pumps, and spray transducers. The delivery devices may also incorporate a propellant or air to promote the formation of foam. The device may also include a means of controlling particle size and spray pattern. The combined solution may be dispensed as an aerosol, a spray, a liquid, a gel, or a foam. In one aspect, the composition may be applied directly to a surface. In another aspect, it may be applied to an applicator such as a sponge or a wipe.

Other embodiments may employ either oxidant or reductant as a dry powder or solution on a nonwoven, woven, synthetic or natural substrate, sponge or cloth and the other component, oxidant or reductant, as a water or other liquid solution that is applied to dissolve or mix with the first component. The solution could be dispensed from a separate container, from a pouch embedded in the substrate or a pouch separated from the substrate by a valve or an irreversibly burstable wall. The liquid contained in the pouch or capsule that is embedded in the substrate may be released when the pouch or capsule is compressed or squeezed. The pouch or capsule may have one exit or more than one exit points for more complete distribution of the liquid onto the substrate. Alternatively, the substrate may contain two or more pouches or capsules wherein at least one pouch or capsule contains the oxidant solution and at least one other pouch or capsule contains the reductant solution. During use the pouches or capsules rupture whereby the two solutions are released and mix within the substrate. In an alternate embodiment each solution could be applied to a different substrate (e.g., nonwoven) and these substrates brought into contact as they are removed from or dispensed from the package.

Other embodiments include substrates that are separated by barriers. For example, a substrate may have two sides separated by an impervious layer, where Part A is contained in liquid form on the first side and part B is contained in liquid form on the second side. The surface to be treated is first wiped with side 1 to release the active and then wiped with side 2 to neutralize the active applied with side 1. Alternatively, a substrate may have two zones that are separated by an impervious layer, where the first zone contains part A in liquid form and the second zone contains part B in liquid form. The first zone comprises the total surface of the substrate. The second zone, separated from the first zone by the impervious barrier, is smaller than the first zone and is located on one side of the substrate. Prior to use, part A cannot mix with part B because the impervious layer prevents the movement of liquids between the two zones. However, when used both zones come into contact with the surface being treated causing part A to mix with part B on said surface.

In another embodiment, the substrate has two zones that are separated by a capillary barrier, where the first zone contains part A in liquid form and the second zone contains part B in liquid form. Prior to use, part A cannot mix with part B because the capillary barrier prevents the movement of liquids between the two zones. However, when used both zones come into contact with the surface being treated causing part A to mix with part B on said surface. The shape of the two zones may vary. In one embodiment the substrate may be divided in half with the capillary barrier down the middle of the substrate. In another embodiment the first zone may be centrally located on the substrate with the second zone surrounding the first zone.

The delivery device may include a means of controlling the mixing ratio of the components. Such devices may rely on the orifice diameter to meter the flow or they may operate by having different pump chamber volumes or rates of pumping. The chambers may connect directly to the delivery device or they may have a dip tube or siphon tube to connect each chamber to the delivery device. In any case, the chambers may be connected to a mixing chamber that is connected to the delivery device, may be connected separately to the delivery device, or may by dispensed through separate devices. For example, a dual chamber system may have a separate siphon tube connecting each chamber to a mixing chamber of a trigger spray head with a single nozzle, or connecting each chamber to separate, adjacent nozzles. In another embodiment, a dual chamber system with a siphon tube connects each chamber to a mixing chamber of a pump dispenser that dispenses the combined solution through a single tube that is easily directed to the point of use.

In one embodiment, the two precursor compositions are in the form of aqueous compositions. In other embodiments, either of, or both of the precursor compositions may be in solid form initially, and then dissolved and/or diluted into water to form an aqueous precursor composition, which can then be combined with the second precursor composition at time of use to produce the inventive composition. In other embodiments, either of, or both of the precursor compositions may be in a thickened liquid or gel form initially and then dissolved and/or diluted into water to form an aqueous precursor composition, which can then be combined with the second precursor composition at time of use to produce the inventive composition. In other embodiments, either of, or both of the precursor compositions may be in a thickened liquid or gel form initially and then mixed with the other composition in the form of a gel or solid to produce the inventive composition.

X. Examples

Without being bound by theory, it is believed that further functionality and both lower and higher concentration ranges of oxidant, reductant and buffer materials can be employed in a range of embodiments according to the present invention than those ranges presented in the following examples. For the purposes of illustration of effect, example embodiments of the invention were in many cases selected in which intermediate hypochlorite compositions were employed solely to enable spectroscopic measurement of the active bleaching species, the levels selected for means of illustration being suitable for direct absorption measurements and thus being limited only with respect to spectroscopic limitations of path length, molar absorbance and saturation (optical quenching in concentrated systems) enabling the level of oxidant to be easily monitored and measured to show trends. These trends illustrating examples are not intended to establish limits of utility on hypochlorite, buffer, or reductant concentration, or ratios.

Example 1—Nitrite

In one embodiment of the invention, nitrite has been found to be a suitable reductant operational across the ranges of concentration illustrated below. Accordingly, in one embodiment of the invention, nitrite has been explored as a reductant as shown in FIG. 2, where the materials and composition parameter ranges explored are as follows: sodium hypochlorite (0.02 wt % to 0.3 wt %), sodium nitrite (0.03 wt % to 0.8 wt %), solution pHs from 6 to 11, wherein the molar ratio of reductant to oxidant (i.e., R/O) varied from 3:1 to 1:2.

Figure 2:
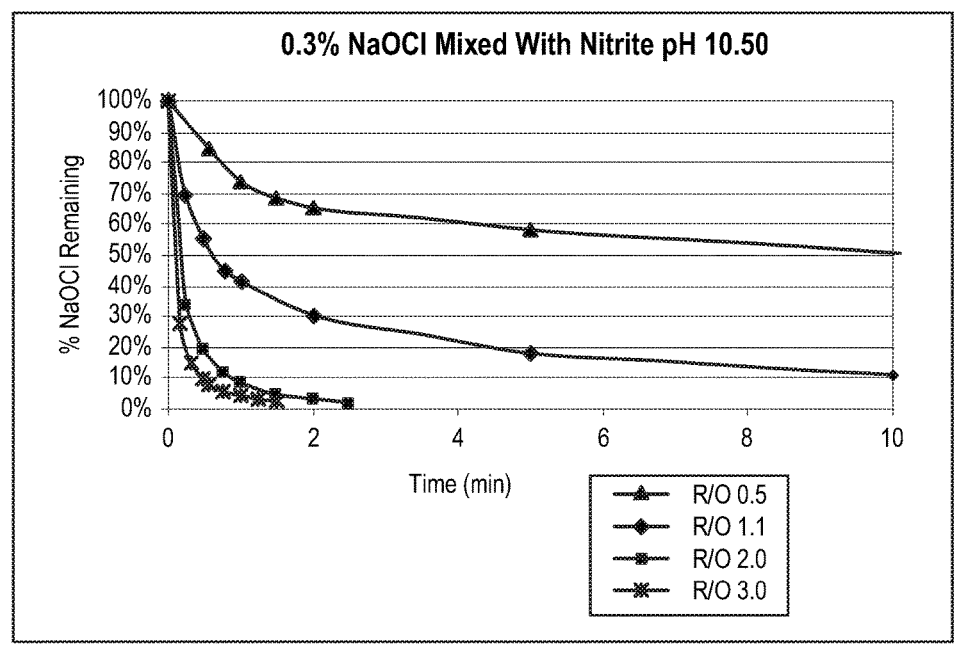
FIG. 2 is a plot of percentage initial hypochlorite remaining as a function of time using a sodium nitrite reductant with no buffer system at various reductant/oxidant ratios.
Figure 3:
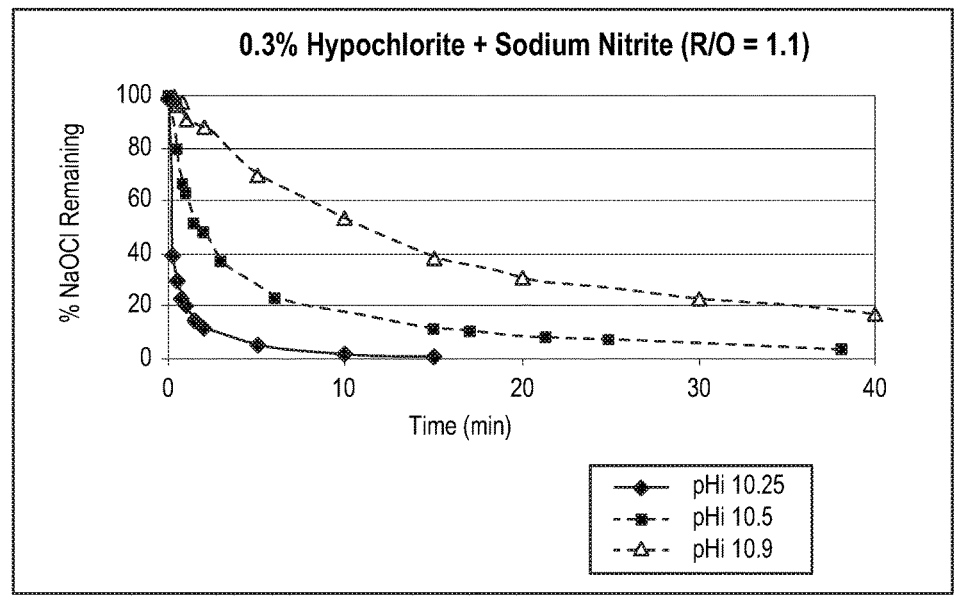
FIG. 3 is a plot of percentage initial hypochlorite remaining as a function of time using a sodium nitrite reductant with no buffer system at various mixture pHs.

In these embodiments, the effect of increasing R/O ratio is clearly evident with higher ratios eliminating hypochlorite more quickly FIG. 2. Further, the importance of controlling pH is evident in FIG. 3, where at higher pHs the reaction proceeds slower in embodiments of the invention where the initial pH is raised.

Figure 4:
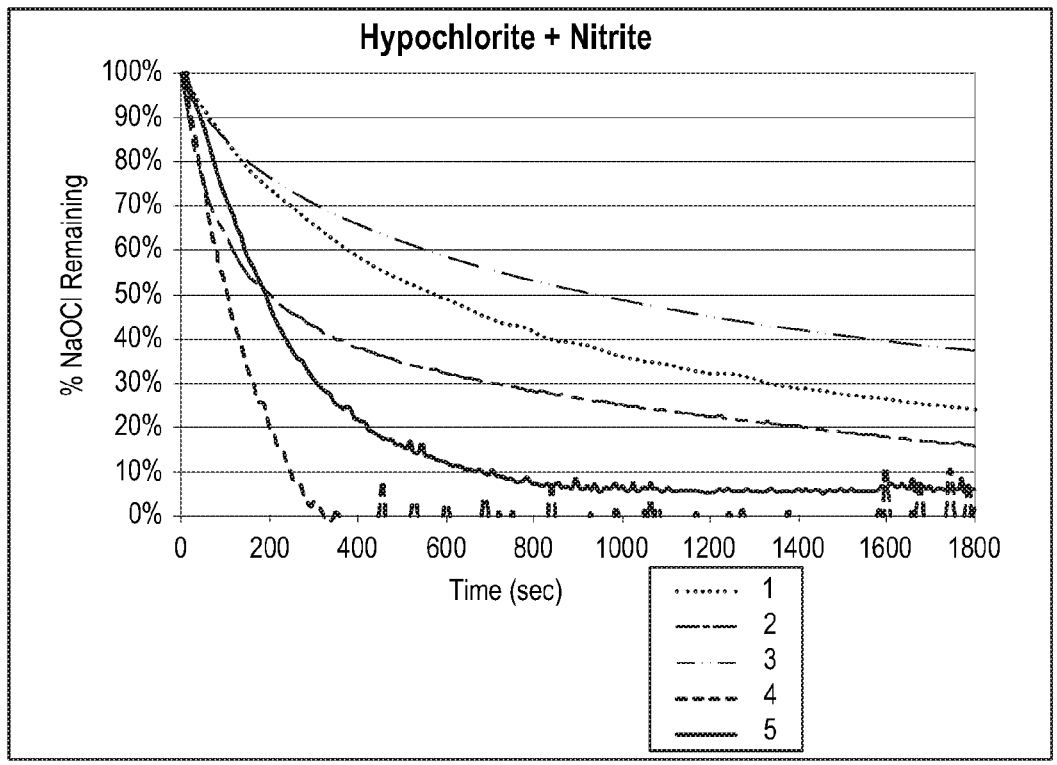
FIG. 4 is a plot of percentage initial hypochlorite remaining as a function of time using a sodium nitrite reductant with a mixed acetate, phosphate, and carbonate buffer system according to several embodiments of the invention.
Figure 5:
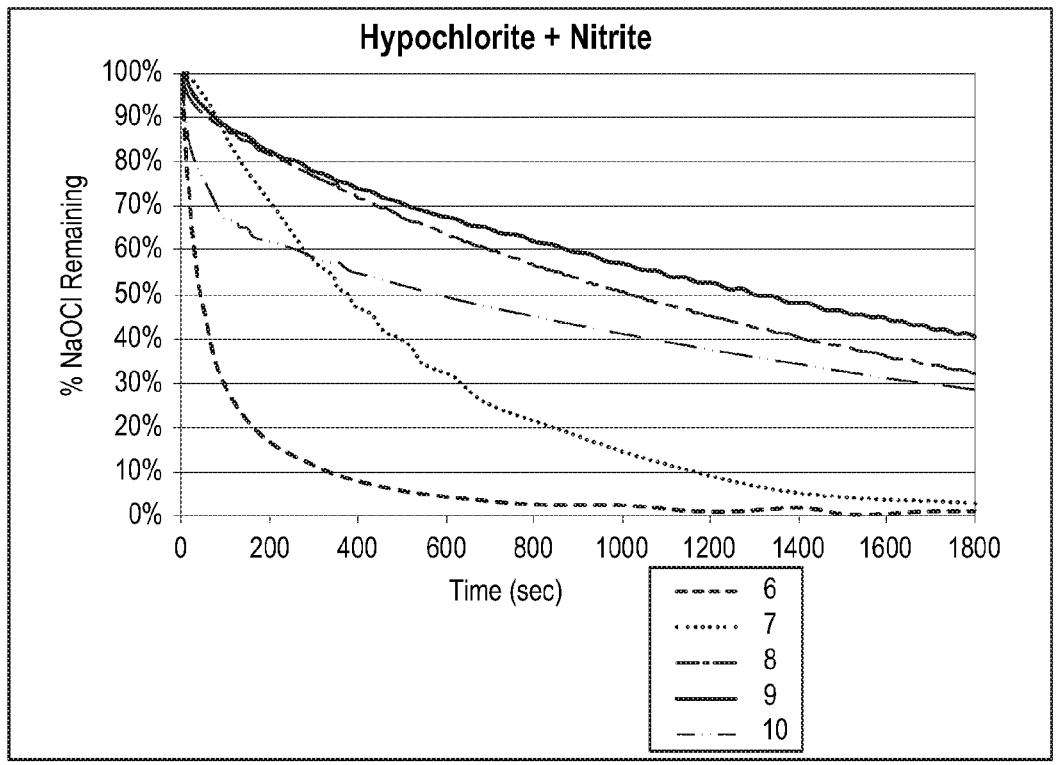
FIG. 5 is a plot of percentage initial hypochlorite remaining as a function of time using a sodium nitrite reductant with a mixed acetate, phosphate, and carbonate buffer system according to several additional embodiments of the invention.

A broad range of conditions may be used to control the rate of hypochlorite consumption (this data may be plotted as hypochlorite ppm if desired). The reaction conditions for FIGS. 4 and 5 are captured in Table 1, in which embodiments of the invention employ use of a buffer of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant.

TABLE 1

| Formula (Traces in FIG. 4 and FIG. 5) | Oxidant[1] (wt %) | Reductant Nitrite (wt %) | Buffered pH | Ratio R/O[2] |
|---|---|---|---|---|
| 1 | 0.048 | 0.045 | 6.0 | 1.0 |
| 2 | 0.033 | 0.030 | 10.0 | 1.0 |

TABLE 1-continued

| Formula (Traces in FIG. 4 and FIG. 5) | Oxidant[1] (wt %) | Reductant Nitrite (wt %) | Buffered pH | Ratio R/O[2] |
|---|---|---|---|---|
| 3 | 0.048 | 0.045 | 11.0 | 1.0 |
| 4 | 0.022 | 0.045 | 8.5 | 2.2 |
| 5 | 0.033 | 0.059 | 7.0 | 1.9 |
| 6 | 0.033 | 0.059 | 10.0 | 1.9 |
| 7 | 0.048 | 0.069 | 8.5 | 1.5 |
| 8 | 0.064 | 0.059 | 7.0 | 1.0 |
| 9 | 0.048 | 0.045 | 8.5 | 1.0 |
| 10 | 0.064 | 0.059 | 10.0 | 1.0 |

[1]Sodium hypochlorite
[2]Molar reductant/Oxidant Ratio (R/O)

Example 2—Fructose

Fructose and other reducing sugars have been found to be suitable for use in the present invention as reductants. Results show an improved utility in higher pH solutions. Without being bound by theory this is believed to be due to reduced reactivity of the sugar toward hypochlorite when the sugar exists in its closed cyclic ester conformation. Elevated pH promotes hydrolysis of the sugar ring to the open configuration which is more reactive with hypochlorite.

Ranges of explored parameters and solution conditions tested were as follows: sodium hypochlorite from 0.02 wt % to 1.0 wt %; fructose from 0.05 wt % to 2.77 wt %, solution pHs from pH 7 to pH 13.4; covering a range of RIO ratios from about 0.7:1 to about 21.7:1.

Figure 6:
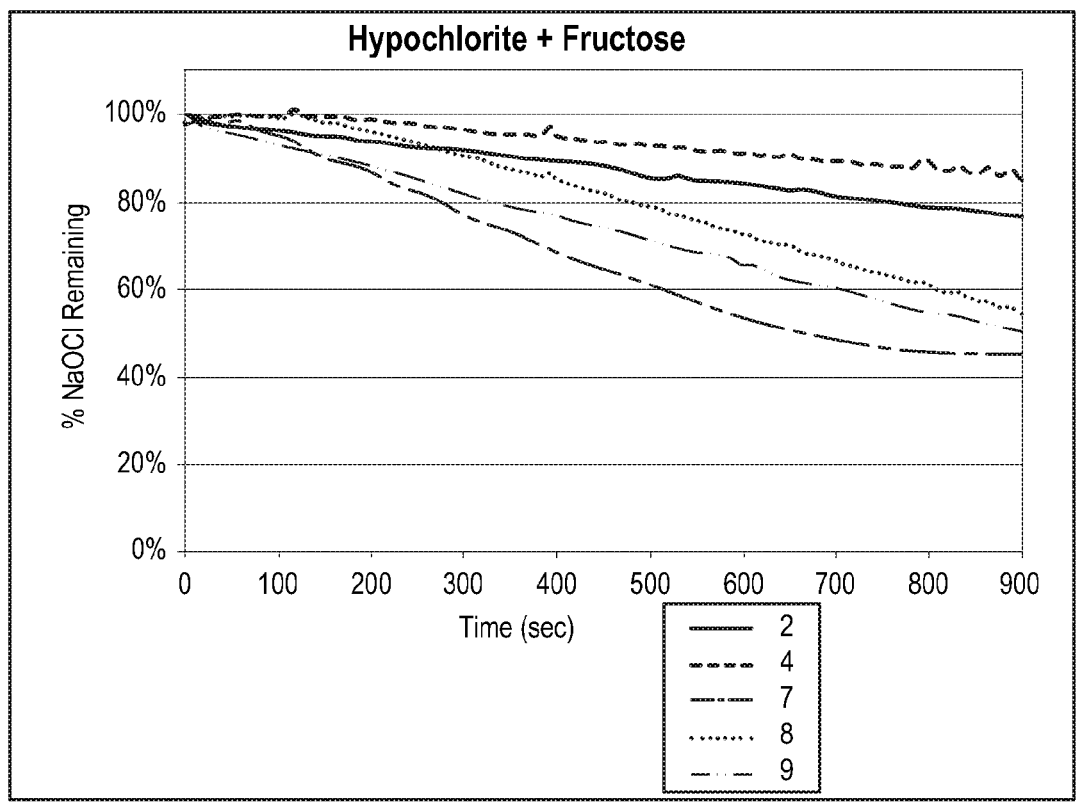
FIG. 6 is a plot of percentage initial hypochlorite remaining as a function of time using a fructose reductant with a carbonate buffer system according to several embodiments of the invention.
Figure 7:
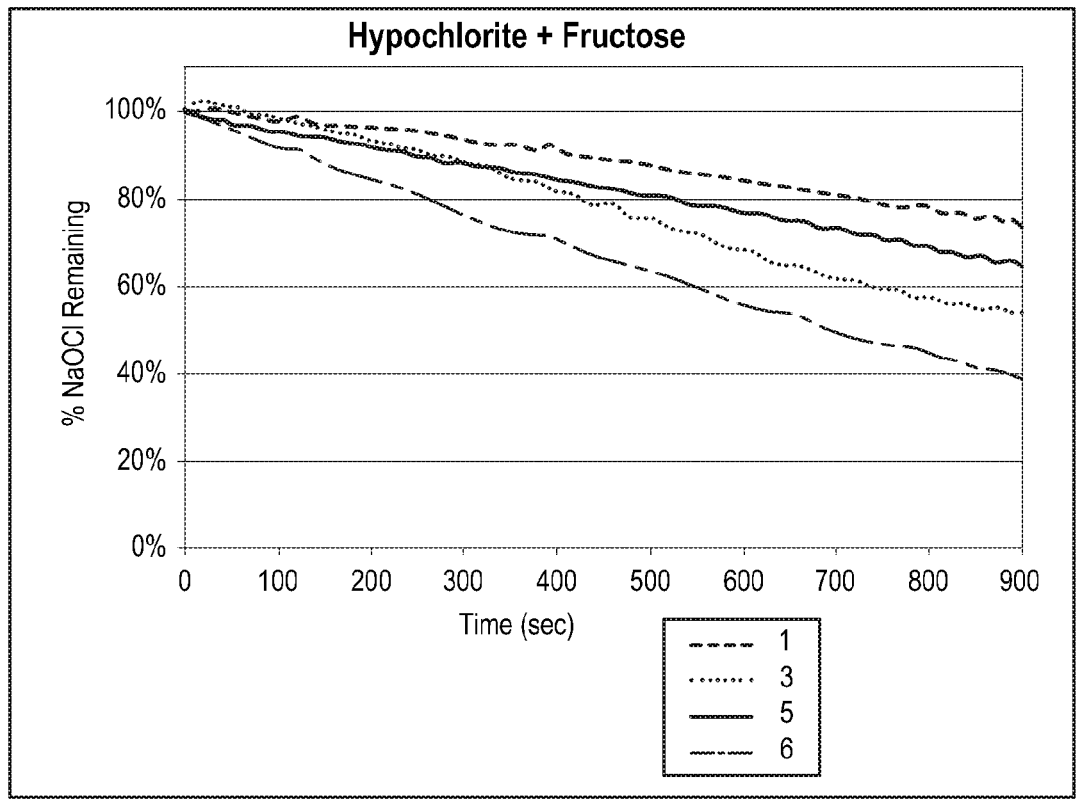
FIG. 7 is a plot of percentage initial hypochlorite remaining as a function of time using a fructose reductant with a carbonate buffer system according to several embodiments of the invention.

In this series of embodiments, at elevated pH a broad range of conditions may be used to control the rate of hypochlorite consumption. A sub-sample of reaction conditions and results are found in Table 2 and FIGS. 6-7.

TABLE 2

| Formula (Traces in FIG. 6 and FIG. 7) | Oxidant (wt %) | Reductant Fructose (wt %) | Buffered pH | Ratio R/O |
|---|---|---|---|---|
| 1 | 0.033 | 0.796 | 12.7 | 10.0 |
| 2 | 0.048 | 1.171 | 9.7 | 10.0 |
| 3 | 0.048 | 1.171 | 13.4 | 10.0 |
| 4 | 0.064 | 0.796 | 13.1 | 5.1 |
| 5 | 0.074 | 1.171 | 12.7 | 6.5 |
| 6 | 0.033 | 1.546 | 13.1 | 19.4 |
| 7 | 0.048 | 1.802 | 12.7 | 15.4 |
| 8 | 0.064 | 1.546 | 13.3 | 10.0 |
| 9 | 0.048 | 1.171 | 13.3 | 10.0 |

Figure 8:
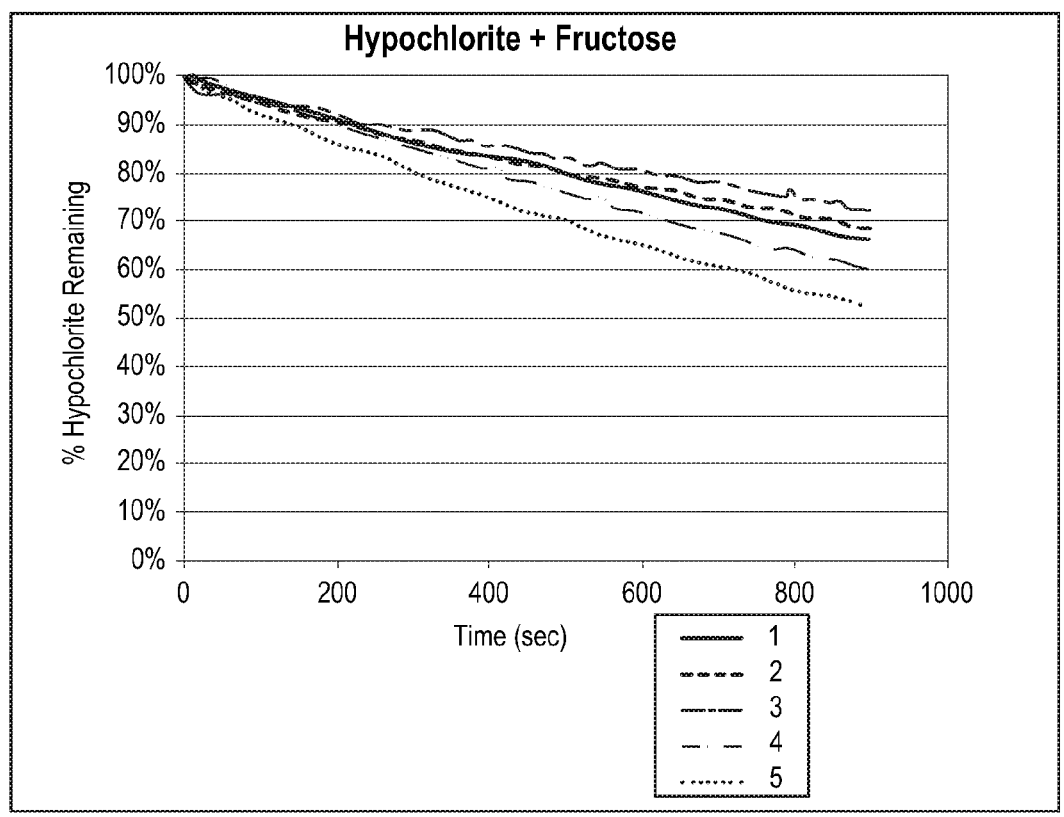
FIG. 8 is a plot of percentage initial hypochlorite remaining as a function of time using a fructose reductant with a mixed acetate, phosphate, and carbonate buffer system according to several additional embodiments of the invention.

Additional utility was found in additional embodiments of the invention employing a lower solution pH as shown in Table 3 below and corresponding FIGS. 8 and 9. These embodiments used a buffer of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant.

TABLE 3

| Formula (Traces in FIG. 8) | Oxidant (wt %) | Reductant Fructose (wt %) | Buffered pH | Ratio R/O |
|---|---|---|---|---|
| 1 | 0.048 | 0.448 | 11.0 | 10.0 |
| 2 | 0.074 | 0.448 | 8.5 | 6.5 |
| 3 | 0.033 | 0.592 | 7.0 | 19.4 |
| 4 | 0.033 | 0.592 | 10.0 | 19.4 |
| 5 | 0.048 | 0.690 | 8.5 | 15.4 |

Figure 9:
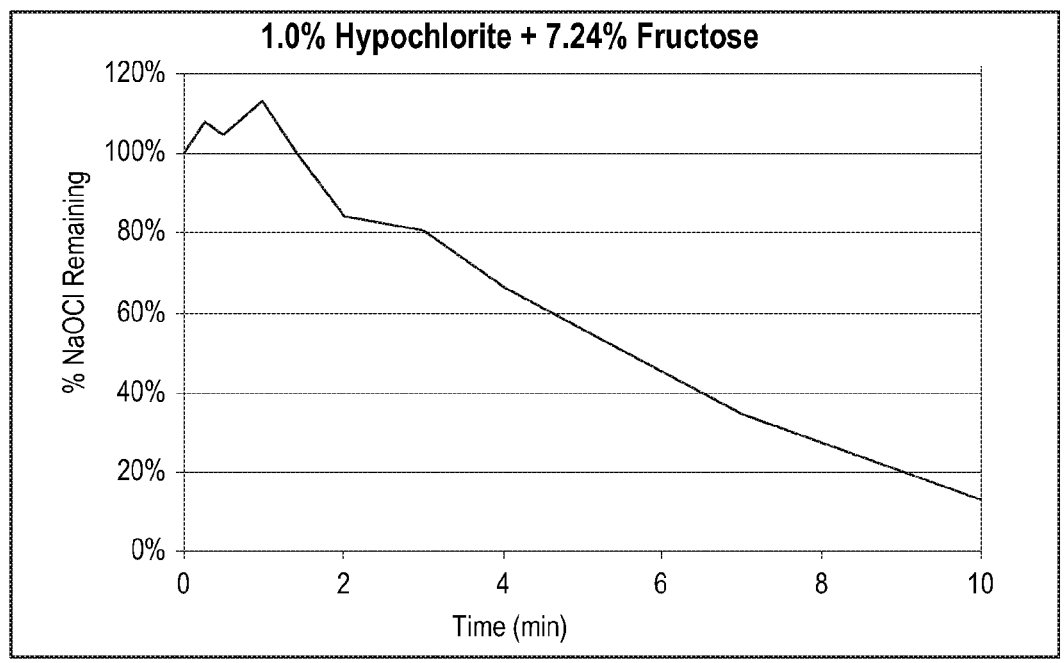
FIG. 9 is a plot of percentage initial hypochlorite remaining as a function of time using a fructose reductant with a carbonate buffer system according to an embodiment of the invention that is configured to effectively quench the oxidant within about 10 minutes.

In yet another embodiment, fructose also can work well at higher hypochlorite concentrations as shown in FIG. 9. The single trace corresponds to a formula containing 1 wt % hypochlorite and 7.24 wt % fructose at an initial starting pH of pH 13.0, which is seen to effectively self-extinguish with respect to the level of remaining oxidant (hypochlorite) within about a 10 minute time period following initial mixing.

Example 3—Chelants

Other embodiments of the invention may employ selected chelants (sequestrants), such as disodium calcium EDTA (CaEDTA), which can be used to limit hypochlorite lifetime in a controlled fashion at lower pH where EDTA alone acts too rapidly in quench the initial hypochlorite concentration. EDTA reacts almost instantly at any pH below 12, but CaEDTA has utility in the near neutral region. Without being bound by theory, it is believed that the calcium salt likely works because the chelation of an aqueous calcium ion by EDTA makes the molecule much less reactive toward hypochlorite. The utility of using pH neutral compounds such as chelants as effective reductants or quenching agents enables ultimate solutions near neutral pH to be employed in the present invention. Again, without being bound by theory, it is believed that chelants act as does the class of other acidic reductants, because at lower pHs the mother ligand (here the partially chelated EDTA species) begins to release calcium ions and revert to a more hypochlorite-reactive acidic EDTA form.

Conditions tested in several illustrative embodiments used a typical calcium ion sequestrant. The ranges of material tested are: sodium hypochlorite from 0.02 wt % to 0.07 wt %; CaEDTA from 0.26 wt % to 3.8 wt %; solution pHs from between pH 6.0 to about pH 9.0; covering a range of reductant (CaEDTA) to oxidant (hypochlorite) ratios of between 1:1 and about 22:1.

Figure 10:
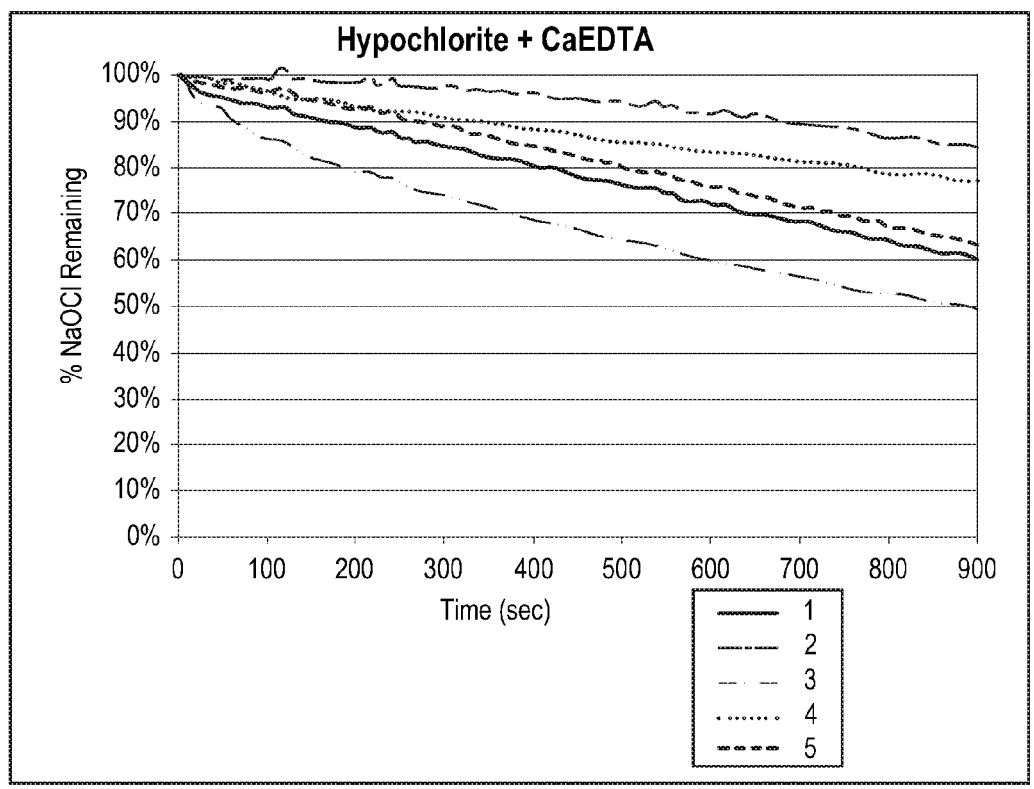
FIG. 10 is a plot of percentage initial hypochlorite remaining as a function of time using CaEDTA as a reductant with a mixed acetate, phosphate, and carbonate buffer system according to several embodiments of the invention.

In these inventive embodiments, various conditions can be used to tune the CaEDTA reaction with hypochlorite. Conditions for the plot shown in FIG. 10 used a buffer of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant, corresponding to Formulas shown in Table 4.

TABLE 4

| Formula (Traces for FIG. 10) | Oxidant (wt %) | Reductant CaEDTA (wt %) | Buffered pH | Ratio R/O |
|---|---|---|---|---|
| 1 | 0.033 | 1.654 | 7.0 | 10.0 |
| 2 | 0.064 | 1.654 | 7.0 | 5.1 |
| 3 | 0.033 | 3.212 | 7.0 | 19.4 |
| 4 | 0.048 | 3.743 | 8.5 | 15.4 |
| 5 | 0.064 | 3.212 | 7.0 | 10.0 |

Example 4—Sorbates

Potassium sorbate represents another chemical class of reductants with tunable reactivity with hypochlorite useful in formulating embodiments of the invention. The control of a soluble sorbate reaction with hypochlorite is very effective at slightly acidic to slightly basic solution pHs, within a wide range of concentrations and ratios of the respective reactants.

Here, example embodiments of the invention were tested covering a range of compositions as follows: sodium hypochlorite between 0.02 wt % to 0.08 wt %, potassium sorbate between 0.06 wt % to 1.5 wt %, at solution pHs of between pH 6 and pH 8.5, covering a range of RIO ratios between about 0.5:1 to about 22:1, as illustrated in Table 5 and Table 6.

TABLE 5

| Formula (Traces for FIG. 11) | Oxidant (wt %) | Reductant K Sorbate (wt %) | Buffered pH | Ratio R/O |
|---|---|---|---|---|
| 1 | 0.033 | 0.066 | 7.0 | 1.0 |
| 2 | 0.048 | 0.098 | 6.0 | 1.0 |
| 3 | 0.064 | 0.066 | 7.0 | 0.5 |
| 4 | 0.074 | 0.098 | 8.5 | 0.7 |
| 5 | 0.033 | 0.129 | 7.0 | 1.9 |
| 6 | 0.064 | 0.129 | 7.0 | 1.0 |

Figure 11:
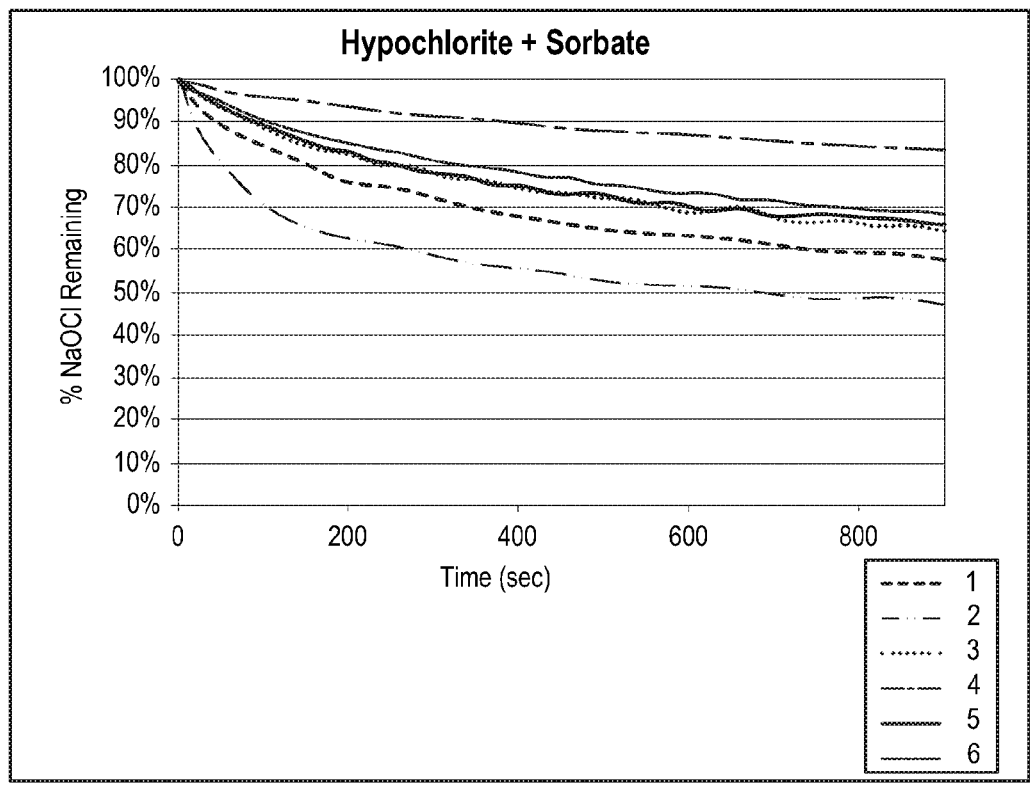
FIG. 11 is a plot of percentage initial hypochlorite remaining as a function of time using potassium sorbate reductant with a mixed acetate, phosphate, and carbonate buffer system according to several embodiments of the invention.

FIG. 11 shows the plot of some experimental conditions with buffers of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant, corresponding to Formulas in Table 5 illustrating selected embodiments of the invention.

TABLE 6

| Formula (Traces for FIG. 12) | Oxidant (wt %) | Reductant K Sorbate (wt %) | Buffered pH | Ratio R/O |
|---|---|---|---|---|
| 1 | 0.033 | 0.664 | 7.0 | 10.0 |
| 2 | 0.064 | 0.664 | 7.0 | 5.1 |
| 3 | 0.022 | 0.976 | 8.5 | 21.7 |
| 4 | 0.074 | 0.976 | 8.5 | 6.5 |
| 5 | 0.048 | 0.451 | 8.5 | 4.6 |
| 6 | 0.048 | 1.502 | 8.5 | 15.4 |

Figure 12:
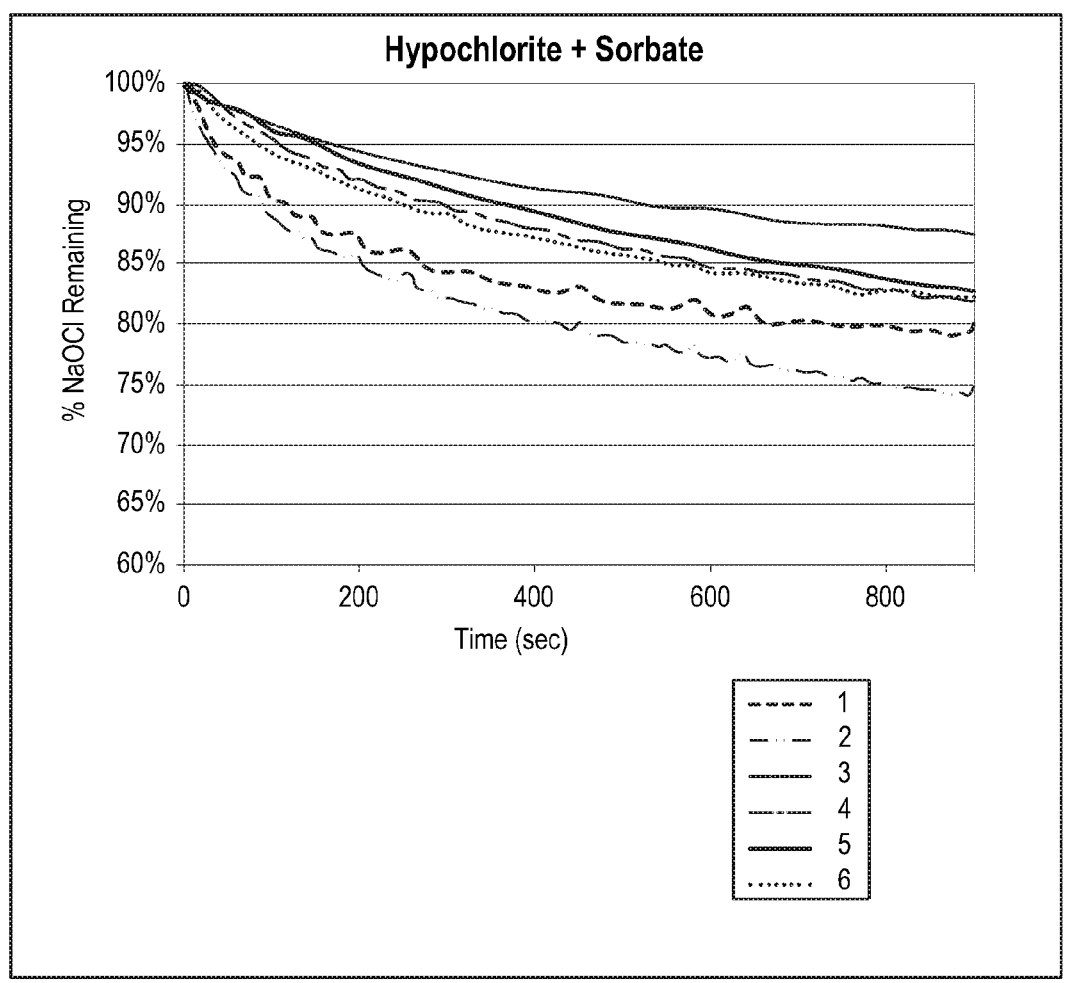
FIG. 12 is a plot of percentage initial hypochlorite remaining as a function of time using potassium sorbate reductant with a mixed acetate, phosphate, and carbonate buffer system according to several additional embodiments of the invention.

FIG. 12 shows the plot of some experimental conditions with buffers of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant, corresponding to Formulas in Table 6.

Example 5—Guanidine Hydrochloride

Figure 13:
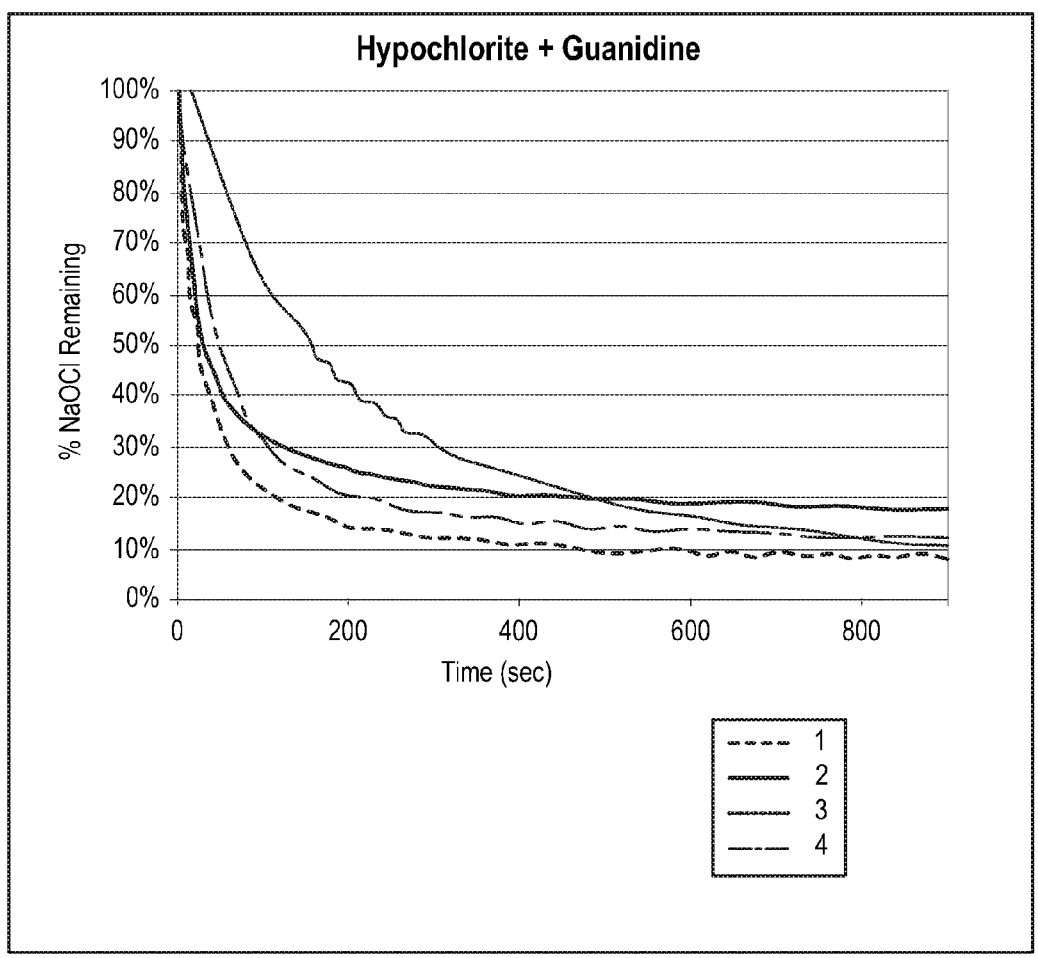
FIG. 13 is a plot of percentage initial hypochlorite remaining as a function of time using guanidine hydrochloride reductant with a carbonate buffer system according to several embodiments of the invention.

In other embodiments of the invention, organic bases such as guanidine hydrochloride may also be used to control hypochlorite levels. Here, levels of components were explored within the limits stated for illustrative purposes: sodium hypochlorite between 0.03 wt % to 0.07 wt %, guanidine hydrochloride between 0.03 wt % to 0.07 wt %, at solution pHs between pH 8.5 and pH 11, covering RIO ratios of between 0.5:1 to about 1:1, as shown in Table 7 and FIG. 13.

TABLE 7

| Formula (Traces for FIG. 13) | Oxidant (wt %) | Reductant Guanidine HCl (wt %) | Buffered pH | Ratio R/O |
|---|---|---|---|---|
| 1 | 0.033 | 0.042 | 10.0 | 1.0 |
| 2 | 0.048 | 0.062 | 11.0 | 1.0 |
| 3 | 0.064 | 0.042 | 10.0 | 0.5 |
| 4 | 0.048 | 0.029 | 8.5 | 0.5 |

Example 6—Organic Acids

Single equivalent organic acids and alpha-carboxylic acids such as lactic acid can be successfully utilized in additional embodiments of the invention in order to limit hypochlorite lifetimes, as illustrated in Table 8. Solution conditions over a select range were tested as follows: sodium hypochlorite between about 0.03 wt % to 0.2 wt %, sodium lactate between 0.06 wt % and 2.42 wt %, at starting solution pHs of between pH 3.5 and pH 9, covering a ratio of lactate/hypochlorite (R/O) of between 1:1 to about 40:1.

TABLE 8

| Formula (Traces in FIG. 14) | Oxidant (wt %) | Reductant Sodium Lactate (wt %) | Buffered pH | Ratio R/O |
|---|---|---|---|---|
| 1 | 0.033 | 0.495 | 7.0 | 10.0 |
| 2 | 0.048 | 0.728 | 6.0 | 10.0 |
| 3 | 0.033 | 0.962 | 7.0 | 19.4 |
| 4 | 0.064 | 0.962 | 7.0 | 10.0 |
| 5 | 0.048 | 0.728 | 8.5 | 10.0 |

Figure 14:
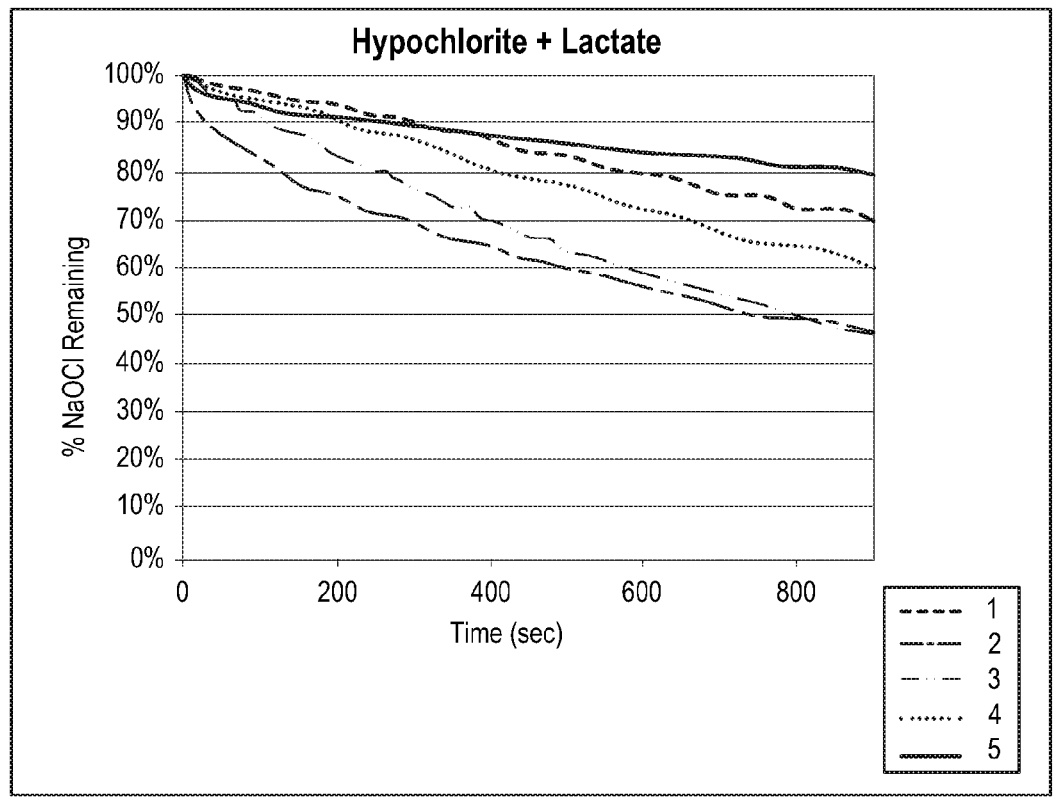
FIG. 14 is a plot of percentage initial hypochlorite remaining as a function of time using sodium lactate as a reductant with a mixed acetate, phosphate, and carbonate buffer system according to several embodiments of the invention.

FIG. 14 shows a plot of experimental conditions with a buffer of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant.

Figure 15:
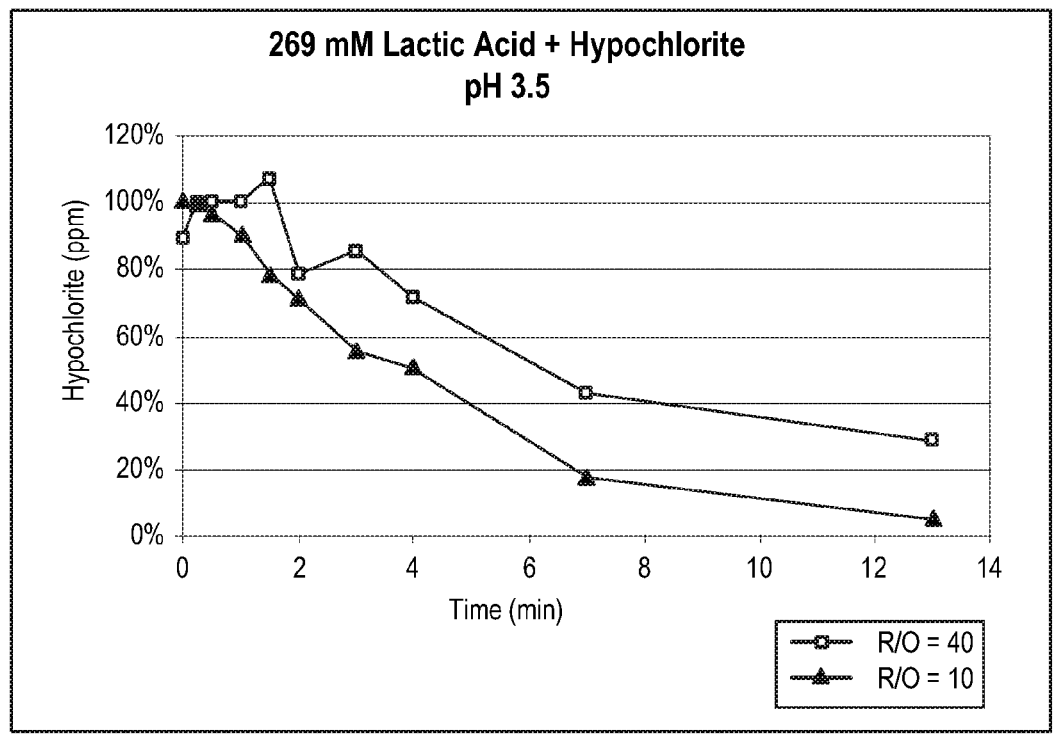
FIG. 15 is a plot of percentage initial hypochlorite remaining as a function of time using sodium lactate as a reductant with acetate buffer system according to several embodiments of the invention at different reductant/oxidant ratios.

Lactic acid will also work at higher hypochlorite concentrations. The formulas tested and shown in FIG. 15 explore use of 2.42 wt % lactic acid with RIO ratios of about 10:1 and about 40:1 with an acetic acid buffer. These embodiments of the invention contain 0.55 wt % of DowFax C10L, a short chain hydrotrope obtained from the Dow Chemical Company.

Example 7—Citric Acid

Citric acid may be used to control the exposure of hypochlorite by time of use mixing in yet further embodiments of the invention as illustrated in Table 9. Solution conditions over a select range where tested as follows: sodium hypochlorite between about 0.03 wt % to 0.2 wt %, Trisodium citrate between 0.06 wt % and 2.42 wt %, at starting solution pHs of between pH 4.0 and pH 9, covering a ratio of citrate/hypochlorite (R/O) of between 1:1 to about 40:1.

TABLE 9

| Formula (Traces in FIG. 16) | Oxidant (wt %) | Reductant Trisodium Citrate (wt %) | Buffered pH | Ratio R/O |
|---|---|---|---|---|
| 1 | 0.033 | 0.495 | 7.0 | 10.0 |
| 2 | 0.048 | 0.728 | 6.0 | 10.0 |

TABLE 9-continued

| Formula (Traces in FIG. 16) | Oxidant (wt %) | Reductant Trisodium Citrate (wt %) | Buffered pH | Ratio R/O |
|---|---|---|---|---|
| 3 | 0.064 | 0.495 | 7.0 | 5.1 |
| 4 | 0.033 | 0.962 | 7.0 | 19.4 |
| 5 | 0.064 | 0.962 | 7.0 | 10.0 |

Figure 16:
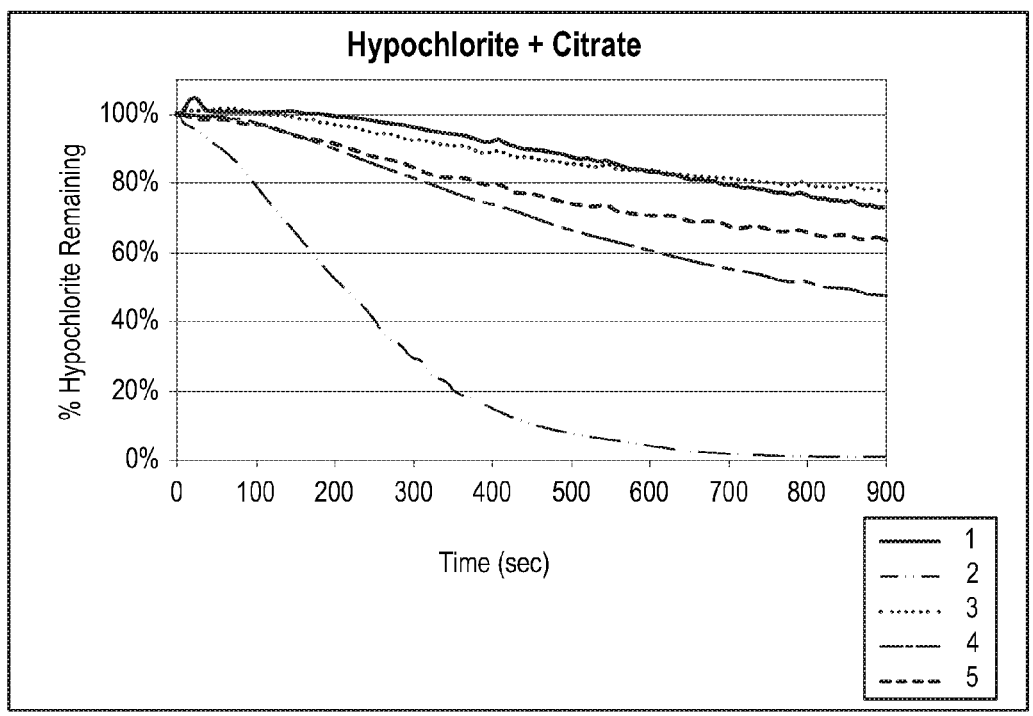
FIG. 16 is a plot of percentage initial hypochlorite remaining as a function of time using sodium citrate as a reductant with a mixed acetate, phosphate, and carbonate buffer system according to several embodiments of the invention.

FIG. 16 shows a plot of experimental conditions with a buffer of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant.

Figure 17:
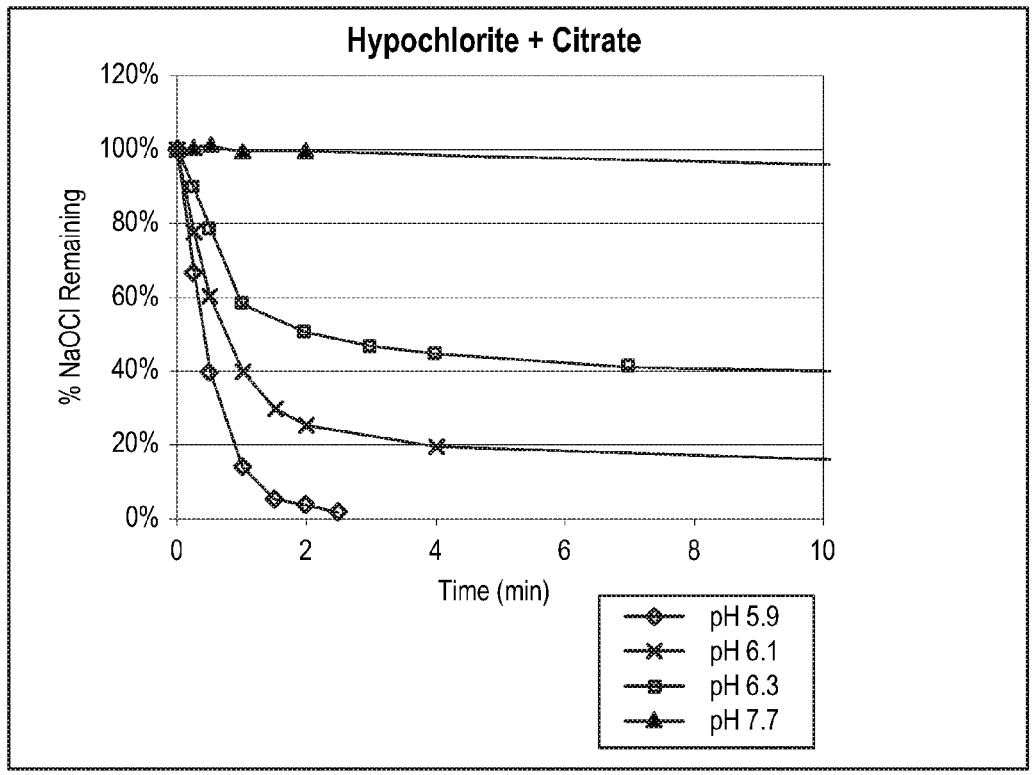
FIG. 17 is a plot of percentage of initial hypochlorite remaining as a function of time using sodium citrate as a reductant with no buffer system according to several embodiments of the invention, illustrating the effect of mix pH on reactivity.
Figure 18:
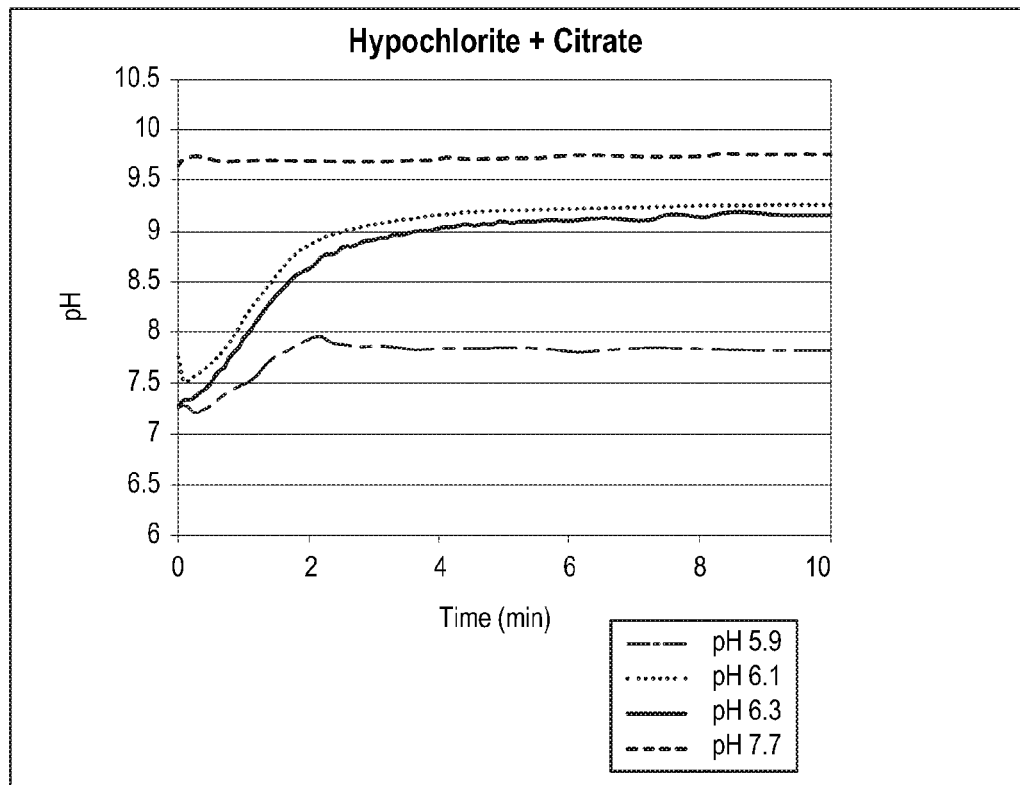
FIG. 18 is a plot of measured solution pH over time of inventive solutions using sodium citrate as a reductant with no buffer system demonstrating that control of hypochlorite lifetime is adversely affected by changing pH in these unbuffered solutions, and that hypochlorite lifetime may be "tuned" to a desired duration without adjusting the reductant/oxidant ratio in a citric acid system.

FIGS. 17 and 18 present embodiments of the invention wherein the inventive principle is illustrated that both the initial pH of the citrate solution and the final mixture pH are important in controlling exposure time to the hypohalite bleach. Additionally, these demonstrate the need for a buffer system not only to determine the initial mixed solution pH but to prevent pH drift as a result of the reaction between the reductant and hypochlorite. The pH of the 3.46 wt % sodium citrate solution was adjusted to the indicated value with hydrochloric acid. The solution was then mixed with an equal volume of 0.4 wt % sodium hypochlorite. It can be seen that by reducing the pH of the initial mixed solution, the rate of hypochlorite consumption may be increased. Further it is illustrated that the pH must not be allowed to rise to ensure complete consumption of all of the hypochlorite. Unbuffered systems with alkaline trending experience a rise in pH over time that correlates to a less favorable slowing in reactivity. In these embodiments of the invention, countering an uncontrolled change or rise in pH may be particularly important to driving the reaction to completion with low ratios of citrate/hypochlorite, which may not be obtainable absent the use of an effective pH controlling buffering system as employed in the described systems.

Embodiments of the invention using citrate quenched bleaching systems were explored over a range of compositional parameters as follows: sodium hypochlorite from 0.01 wt % to about 3 wt %; sodium citrate from about 0.18 wt % to 5.16 wt %; at solution pHs of about pH 4 to pH 10, covering a ratio of reductant/oxidant of from about 1:1 to about 20:1.

Traces in FIGS. 17 and 18 show the tunability of these embodiments and the importance of the additional buffer system to prevent excessively large changes in solution pH with respect to the initial starting pH throughout the time period corresponding to the extinction of the hypochlorite active. The initial pH of the buffer side is indicated in the legend. In this particular embodiment of the invention, FIG. 18 illustrates the need for the inventive approach to keep the pH below pH 8, where only small changes in net hydronium ion ($H_3O^+$) and hydroxide ion (OH) can otherwise effect large (>pH 3 to 5 unit) swings in solution pH.

Example 8—Tetrathionate

In another embodiment of the invention, tetrathionate provides good control over hypochlorite exposure in the neutral to alkaline solution pH range. Tetrathionate allows good control over the pH of the mixed solution by avoiding the instant reactions and pH jumps observed with other sulfur containing reducing agents like thiosulfate or sulfite.

Figure 19:
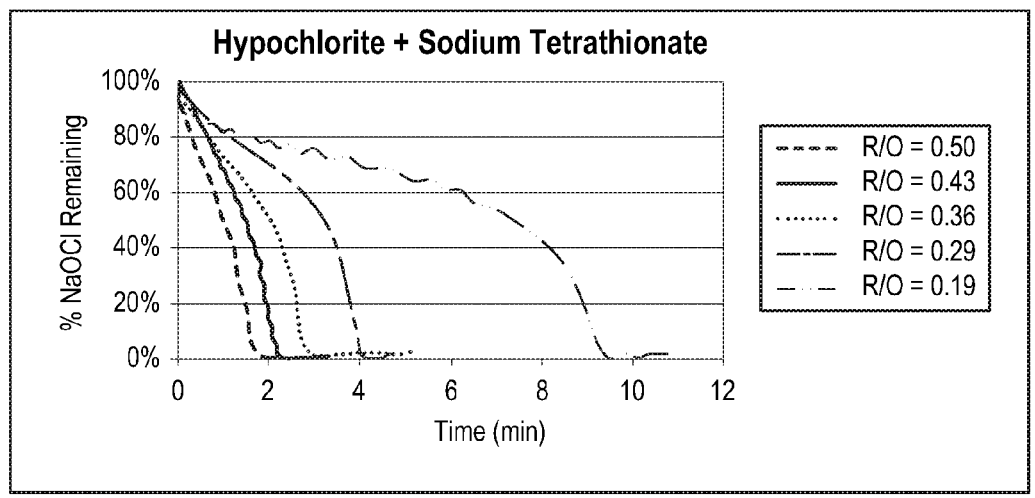
FIG. 19 is a plot of percentage initial hypochlorite remaining as a function of time using sodium tetrathionate as a reductant with a mixed succinate, phosphate, and carbonate buffer system according to several embodiments of the invention at various reductant/oxidant ratios.
Figure 20:
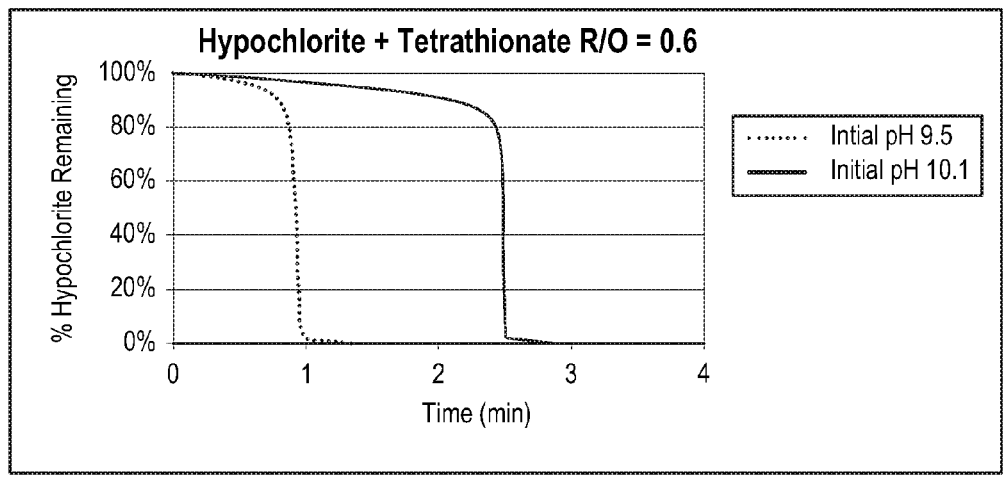
FIG. 20 is a plot of percentage initial hypochlorite remaining as a function of time using sodium tetrathionate as a reductant with a mixed succinate phosphate, and carbonate buffer system according to several additional embodiments of the invention at various reductant/oxidant ratios.

FIGS. 19 and 20 show the impact of mixing ratio on hypochlorite exposure over a range of illustrative embodiments. The initial bleach solution was buffered at pH 10.2 with 1.27 wt % sodium carbonate and the tetrathionate was buffered at pH 6.7 with a 0.32 wt % succinate, 0.48 wt % phosphate buffer prior to mixing. In these embodiments, a 1:1 vol:vol mixing ratio produced the hypochlorite exposure curves shown in FIGS. 19-20.

Compositional ranges explored experimentally were as follows: sodium hypochlorite from 0.01 wt % to about 0.74 wt %; sodium tetrathionate from about 0.41 wt % to about 1.22 wt %, with solution pHs of pH 8 to pH 11, covering a range of RIO ratios of between 0.1:1 to about 5.3:1.

The effect of initial pH of the mixed solution is demonstrated in FIG. 19. In these embodiments of the invention, the sodium tetrathionate was buffered at pH 7.87 or pH 9.51 with 0.26 wt % sodium carbonate. The initial pH of the solutions when mixed at a ratio of 1:1 vol:vol was 9.5 and 10.1, respectively. It is to be noted that the initial pH of the mixture may be used to control the length of hypochlorite exposure in the present inventive systems, providing a means of adjusting the benefit period of hypochlorite activity as desired for its intended application.

Example 9—Thiosulfate

In yet another embodiment of the invention, thiosulfate may be utilized to provide control over hypochlorite exposure. Without being bound by theory, it is believed that thiosulfate behaves similarly to tetrathionate with the exception of a rapid initial pH increase that occurs directly upon mixing concurrent with the instantaneous loss of a molar equivalent of hypochlorite. The remaining hypochlorite reacts slowly in a conditionally dependent fashion until a rapid decrease in pH is observed. This rapid decline in pH correlates with the consumption of all of the remaining hypochlorite. In these illustrative embodiments of the invention, by addition of a buffer system to the thiosulfate the pH may be controlled solely by the mixing of the two materials and precludes the necessity of a subsequent pH adjustment step.

Compositional ranges and conditions that were explored experimentally in these embodiments of the invention are as follows: sodium hypochlorite from about 0.01 wt % to about 0.74 wt %; sodium thiosulfate from about 0.1 wt % to about 11.16 wt %; solution pH of about pH 8 to about pH 11, covering a range of ratios of reductant/oxidant of about 1:1 to about 4:1.

Figure 21:
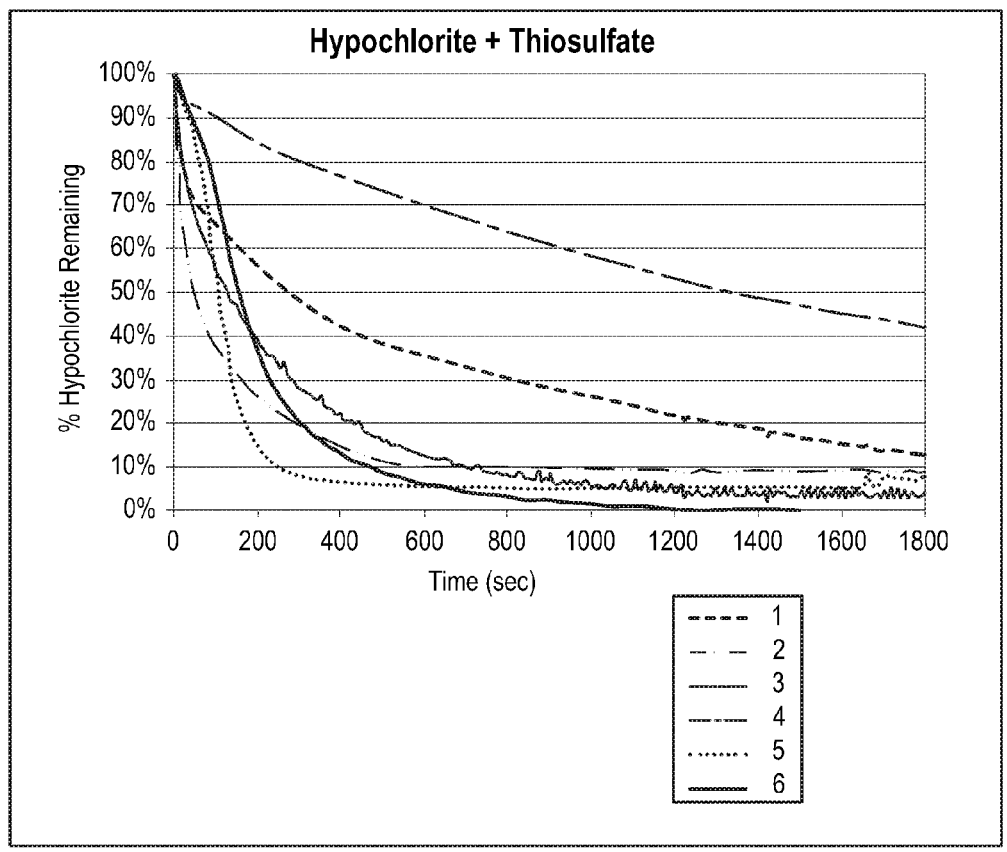
FIG. 21 is a plot of percentage initial hypochlorite remaining as a function of time using sodium thiosulfate reductant with a mixed acetate, phosphate, and carbonate buffer system.

In Table 10 and FIG. 21 experimental conditions include a buffer of 0.08 wt % sodium acetate, 0.14 wt % sodium phosphate dibasic, 0.08 wt % sodium bicarbonate and 0.11 wt % sodium carbonate, adjusted prior to mixing with sufficient hydrochloric acid so that the indicated pH results upon mixing the oxidant and reductant.

TABLE 10

| Formula (Traces in FIG. 21) | Oxidant (wt %) | Reductant Sodium thiosulfate (wt %) | Buffered pH | Ratio R/O |
|---|---|---|---|---|
| 1 | 0.033 | 0.066 | 10.0 | 1.0 |
| 2 | 0.048 | 0.073 | 11.0 | 1.0 |
| 3 | 0.064 | 0.050 | 7.0 | 0.5 |
| 4 | 0.064 | 0.050 | 10.0 | 0.5 |
| 5 | 0.074 | 0.073 | 8.5 | 0.7 |
| 6 | 0.048 | 0.034 | 8.5 | 0.5 |

Figure 22:
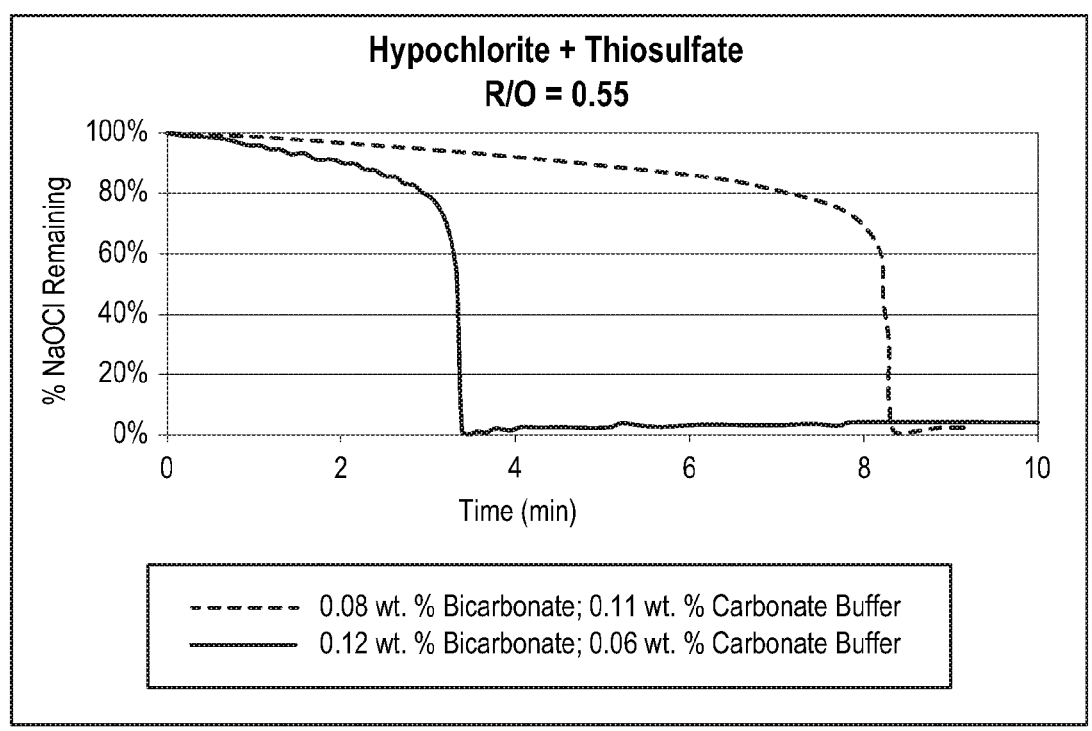
FIG. 22 is a plot of percentage initial hypochlorite remaining as a function of time using sodium thiosulfate reductant with a carbonate buffer system.

The composition of the buffer can be used to control the hypochlorite exposure without an additional pH adjusting step. In FIG. 22, the advantages of the present inventive buffering system are shown in several embodiments of the invention with respect to controlling the transient hypochlorite lifetime for a solution of hypochlorite and thiosulfate with an R/O ratio of about 0.55:1. The 0.60 wt % hypochlorite solution used a carbonate buffer and the 1.09 wt % sodium thiosulfate solution used a combination of 2.59 wt % sodium succinate, 0.28 wt % sodium phosphate dibasic and a 0.24 wt % sodium phosphate monobasic buffer. The thiosulfate solution has a pH of 6.7. The pH of the bleach solution is determined by the carbonate buffer. Hypochlorite solutions with 0.12 wt % bicarbonate with 0.06 wt % carbonate have a pH of 9.7 (solid line in FIG. 22). Hypochlorite solutions with 0.08 wt % bicarbonate and 0.11 wt % carbonate have a pH of 10.1 (dashed line in FIG. 22). The composition of buffer present in the solutions prior to mixing controls the exposure time of hypochlorite.

Example 10—Mixture of Reducing Agents

Another embodiment of the invention may employ a combination of reducing agents to control the hypochlorite exposure time at a desired pH. An example of such as system employs both Nitrite and Fructose as reductants. Without being bound by theory it is believed that such a combination would be advantageous to maintain a constant and rapid rate of hypochlorite consumption.

Figure 23:
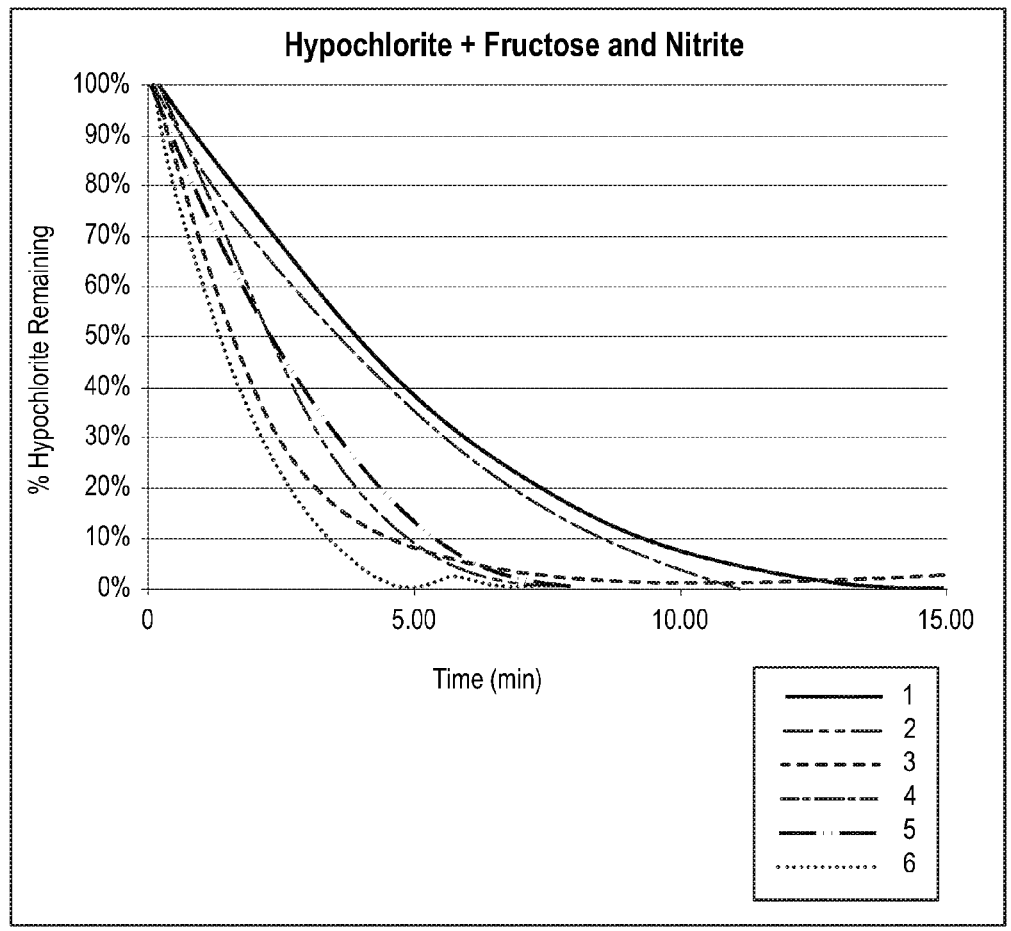
FIG. 23 is a plot of percentage initial hypochlorite remaining as a function of time using a mixture of fructose and nitrite reductants with a carbonate buffer system.

Levels of components were explored within the limits stated for illustrative purposes: sodium hypochlorite between 0.4 wt % to 0.8 wt %, Fructose at 5.8%, Nitrite between 0.07 wt % to 1.5 wt %, at solution pH of pH 11.5, covering R/O ratios of between 3:1 to about 6:1 for fructose, and 1:1 to about 4:1 for Nitrite as shown in Table 11 and FIG. 23.

TABLE 11

| Formula | Oxidant (wt %) | Reductant Frutose - Nitrite (wt %) | | Buffered pH | Ratio R/O | |
|---|---|---|---|---|---|---|
| | | Fructose | Nitrite | | Fructose | Nitrite |
| 1 | 0.800 | 5.808 | 0.000 | 11.5 | 3.0 | 0.0 |
| 2 | 0.800 | 5.808 | 0.741 | 11.5 | 3.0 | 1.0 |
| 3 | 0.800 | 5.808 | 1.483 | 11.5 | 3.0 | 2.0 |
| 4 | 0.400 | 5.808 | 0.000 | 11.5 | 6.0 | 0.0 |
| 5 | 0.400 | 5.808 | 0.741 | 11.5 | 6.0 | 2.0 |
| 6 | 0.400 | 5.808 | 1.483 | 11.5 | 6.0 | 4.0 |

FIG. 23 shows hypochlorite lifetimes resulting from the conditions detailed in Table 11. The buffer system for all solutions in table 11 was 1.0% sodium carbonate with 0.25% sodium hydroxide.

Product Examples

The above examples explored a variety of embodiments of the present invention that can be exploited to achieve a desired beneficial effect, showing details of tuning the various parameters of initial controlled solution pH and reductant/oxidant ratio. In addition, some practical product examples are presented here as non-limiting embodiments of inventive compositions useful for commercial cleaning products and solutions by way of illustration.

Example 11—Mold and Mildew Remover

Tables 12 and 13 show non-limiting embodiments of mold and mildew removers using compositions of the present invention.

TABLE 12

| | Product Composition (wt %)[1] | | | | |
|---|---|---|---|---|---|
| Product No. | 1 | 2 | 3 | 4 | 5 |
| Reductant/Oxidant Ratio (R/O) | 0.33 | 0.67 | 0.25 | 0.25 | 0.25 |
| Sodium Hypochlorite | 2.23 | 2.23 | 2.23 | 2.23 | 2.23 |
| Sodium Bicarbonate | 0.00 | 0.00 | 0.55 | 2.10 | 1.68 |
| Sodium Carbonate | 1.59 | — | 0.90 | 3.71 | 4.24 |
| Sodium Tetrathionate | 2.70 | 5.40 | 2.03 | 2.03 | 2.03 |
| Succinic Acid | 0.30 | — | — | — | 0.24 |
| Sodium Succinate | 0.41 | 0.81 | — | — | 0.49 |
| DowFax C10L | 0.55 | 0.55 | 0.55 | 0.55 | 0.55 |
| pH mixture[2] | 10.6 | 10.5 | 10.5 | 10.5 | 10.5 |

[1]Weight % based on 100% active, unless otherwise noted
[2]pH of mixture of R and O precursor compositions

TABLE 13

| | Product Composition (wt %) | | | | |
|---|---|---|---|---|---|
| Product No. | 6 | 7 | 8 | 9 | 10 |
| Reductant/Oxidant Ratio (R/O) | 2.5 | 2.5 | 5 | 1.2 | 10 |
| Sodium Hypochlorite | 0.37 | 0.37 | 0.19 | 0.37 | 0.37 |
| Sodium Bicarbonate | — | — | — | — | — |
| Sodium Carbonate | 1.06 | — | — | 1.06 | 1.06 |
| Trisodium Citrate | 3.23 | 3.23 | 3.23 | 1.55 | 12.90 |
| Succinic Acid | 2.13 | 1.18 | 0.59 | 3.54 | 1.54 |
| Sodium Succinate | — | 1.62 | 2.43 | 0.81 | 2.92 |
| DowFax C10L | 0.55 | 0.55 | 0.55 | 0.55 | 0.50 |
| pH mixture | 6 | 6 | 6.5 | 5.25 | 7.04 |

Example 12—Acid Bathroom Cleaner with Hypochlorite

Table 14 shows non-limiting embodiments of an acidic bathroom cleaner using compositions according to the present invention.

TABLE 14

| | Product Composition (wt %) | | | | |
|---|---|---|---|---|---|
| Product No. | 11 | 12 | 13 | 14 | 15 |
| Reductant/Oxidant Ratio (R/O) | 2.5 | 5 | 25 | 10 | 100 |
| Sodium Hypochlorite | 0.37 | 0.19 | 0.04 | 0.37 | 0.04 |
| Sodium Carbonate | 0.53 | 0.26 | 0.53 | 1.06 | 1.59 |
| Lactic acid | 1.13 | 1.13 | 1.13 | 4.50 | 4.50 |
| Succinic Acid | 2.36 | 0.59 | 0.30 | — | — |
| Sodium Succinate | — | 0.81 | 0.81 | 2.11 | 3.08 |
| DowFax C10L | 0.55 | 0.55 | 0.55 | 0.55 | 0.55 |
| pH mixture | 4 | 5 | 5.1 | 4.5 | 5.1 |

Example 13—Stain or Spot Remover for Carpets or Laundry

Tables 15 and 16 show non-limiting embodiments of a spot and/or stain remover composition suitable for use on carpets or as a laundry stain pretreatment according to the present invention.

TABLE 15

| | Product Composition (wt %) | | | |
|---|---|---|---|---|
| Product No. | 16 | 17 | 18 | 19 |
| Reductant/Oxidant Ratio (R/O) | 3.2 | 12 | 24 | 120 |
| Sodium Hypochlorite | 0.19 | 0.19 | 0.19 | 0.04 |
| Sodium Hydroxide | 1.00 | 1.00 | 1.00 | 0.20 |
| Sodium Carbonate | 0.53 | 1.06 | 5.30 | 10.60 |
| Fructose | 1.44 | 5.40 | 10.81 | 10.81 |
| DowFax C10L | 5.0 | 5.0 | 5.0 | 5.0 |
| pH mixture | 13.4 | 13.4 | 13.4 | 12.7 |

TABLE 16

| | Product Composition (wt %) | | | |
|---|---|---|---|---|
| Product No. | 20 | 21 | 22 | 23 |
| Reductant/Oxidant Ratio (R/O) | 1 | 0.2 | 2 | 0.5 |
| Sodium Hypochlorite | 0.04 | 0.19 | 0.37 | 0.74 |
| Sodium Bicarbonate | 0.08 | — | 0.08 | — |
| Sodium Carbonate | 0.11 | 0.53 | 10.60 | 3.18 |
| Guanidine HCL | 0.05 | 0.05 | 0.96 | 0.48 |
| Sodium Phosphate monobasic | 20.00 | 30.00 | 10.00 | 10.00 |
| Sodium Phosphate dibasic | — | 0.14 | 0.14 | 0.14 |
| DowFax C10L | 5.0 | 5.0 | 5.0 | 5.0 |
| pH mixture | 7.5 | 8.1 | 11.9 | 11.7 |

Example 14—Hand Sanitizer

Table 17 shows non-limiting embodiments of a hand sanitizer composition according to the present invention suitable for use on hands, skin, nails and epidermis for convenient disinfection and/or presurgical preparation.

TABLE 17

| | Product Composition (wt %) | | | | |
|---|---|---|---|---|---|
| Product No. | 24 | 25 | 26 | 27 | 28 |
| Reductant/Oxidant Ratio (R/O) | 100 | 5 | 1 | 2 | 0.25 |
| Sodium Hypochlorite | 0.01 | 0.07 | 0.15 | 0.30 | 0.30 |
| Sodium Bicarbonate | — | 0.04 | 0.04 | 0.04 | 0.04 |
| Sodium Carbonate | 0.11 | 0.11 | 0.21 | 0.42 | 0.42 |
| Sodium Ascorbate | 1.98 | 0.99 | 0.40 | 1.58 | 0.20 |
| Sodium Phosphate monobasic | 0.24 | 0.24 | 0.24 | 0.30 | 0.60 |
| Sodium Phosphate dibasic | 0.14 | — | 0.14 | 0.14 | 0.14 |
| Propylene glycol | 1.0 | 1.0 | 1.0 | 1.0 | 1.0 |
| pH mixture | 7.6 | 7.7 | 9.1 | 10 | 8.3 |

Example 15—Dilutable Hard Surface Cleaner

Table 18 shows non-limiting embodiments of dilutable hard surface cleaning compositions according to the present invention suitable for use on treating surfaces such as countertops, floors, walls, stove surfaces, tile, grout and bathroom surfaces and the like.

TABLE 18

| | Product Composition (wt %) | |
|---|---|---|
| Product No. | 29 | 30 |
| Reductant/Oxidant Ratio (R/O) | 2 | 2 |
| Sodium Hypochlorite | 4.47 | 0.45 |
| Sodium Bicarbonate | — | — |
| Sodium Carbonate | 6.36 | 0.64 |
| Trisodium Citrate | 30.97 | 3.10 |
| Succinic Acid | 2.36 | 0.24 |
| Sodium Succinate | 3.24 | 0.32 |
| Sodium Lauryl Sulfate | 10.0 | 1.0 |
| pH mixture[1] | 10 | 10 |
| Dilution ratio[2] | 1:100 | 1:10 |

[1]pH of mixture of R and O precursor compositions
[2]Subsequent dilution of mixed compositions into water at indicated volume:volume ratio

Example 16—Through the Wash Dilutable Laundry Additive

Table 19 shows non-limiting embodiments of a "through the wash" dilutable laundry additive for bleaching, whitening, stain removal and potential laundry disinfection, according to the present invention.

TABLE 19

| | Product Composition (wt %) | |
|---|---|---|
| Product No. | 31 | 32 |
| Reductant/Oxidant Ratio (R/O) | 1.4 | 1.1 |
| Sodium Hypochlorite | 5.40 | 5.40 |
| Sodium Carbonate | 3.18 | 0.21 |
| Sodium Nitrite | 6.90 | 5.52 |
| Sodium Lauryl Sulfate | 1.00 | 1.00 |
| pH mixture[1] | 11.9 | 11.3 |
| Dilution ratio[2] | 1:300 | 1:300 |
| pH after dilution[3] | 10.58 | 9.9 |

[1]pH of mixture of R and O precursor compositions
[2]Subsequent dilution of mixed compositions into water at indicated volume:volume ratio
[3]pH of diluted composition after mixing of R and O precursor compositions and dilution with water at prescribed dilution ratio

Example 17—Surface Disinfectant

Table 20 shows non-limiting embodiments of direct use surface disinfectant compositions according to the present invention.

TABLE 20

| | Product Composition (wt %) | | | | | |
|---|---|---|---|---|---|---|
| Product No. | 33 | 34 | 35 | 36 | 37 | 38 |
| Reductant/Oxidant Ratio (R/O) | 1.27 | 1.27 | 0.67 | 0.67 | 3.33 | 24 |
| Sodium Hypochlorite | 0.22 | 0.22 | 0.22 | 0.22 | 0.11 | 0.04 |
| Sodium Carbonate | 0.08 | 0.08 | 0.08 | 0.08 | 0.08 | 0.08 |
| Trisodium Citrate | 0.98 | 0.98 | 0.52 | 0.52 | 1.29 | 3.10 |
| Succinic Acid | 0.35 | 0.35 | 0.47 | 0.47 | 0.24 | 0.18 |
| Sodium Succinate | — | — | 0.08 | 0.08 | 0.49 | 0.57 |
| Potassium Bromide | — | 0.08 | — | 0.04 | — | — |
| Sodium Lauryl Sulfate | 10.0 | 10.0 | 1.0 | 1.0 | 1.0 | 1.0 |
| pH mixture | 5.7 | 5.7 | 5.3 | 5.3 | 6.2 | 6.3 |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A method for treating a surface, the method comprising:
providing a two-part composition comprising:
an oxidant first part comprising a hypohalous acid or a hypohalite; and
a reductant second part comprising guanidine hydrochloride, wherein the guanidine hydrochloride comprises from 0.03% to 1.0% by weight of the two-part composition,
wherein the first and second parts are initially separate;
wherein a molar ratio of the reductant to the oxidant is 0.5:1 to about 1:1; and
mixing the oxidant first part with the reductant second part to form a mixed composition, wherein the mixed composition has a pH from 8.5 to 11; and
contacting the mixed composition with a surface to provide oxidizing benefits to the surface whereby the oxidant is reduced by the reductant to prevent damage caused by prolonged exposure to the hypohalous acid or the hypohalite.

2. The method of claim 1, wherein the hypohalous acid or the hypohalite comprises from about 0.001% to about 10% by weight of the two-part composition.

3. The method of claim 1, wherein the hypohalous acid or the hypohalite comprises from about 0.005% to about 5% by weight of the two-part composition.

4. The method of claim 1, wherein the hypohalous acid or the hypohalite comprises from about 0.005% to about 0.2% by weight of the two-part composition.

5. The method of claim 1, further comprising a pH buffer comprising at least one member of an organic acid, a phosphate, a bicarbonate or a carbonate.

6. The method of claim 5, wherein the buffer is carbonate.

7. The method of claim 5, wherein the second part comprises the buffer.

8. The method of claim 1, wherein the oxidant is hypochlorite.

9. The method of claim 1, wherein the surface is a hard surface.

10. The method of claim 1, wherein the surface is a soft surface.

11. A method for treating a surface, the method comprising:
providing a two-part composition comprising:
an oxidant first part comprising a hypohalous acid or a hypohalite, the hypohalous acid or the hypohalite comprising from about 0.001% to about 10% by weight of the two-part composition; and
a reductant second part comprising guanidine hydrochloride, the guanidine hydrochloride comprising from 0.03% to 1.0% by weight of the two-part composition,
wherein the first and second parts are initially separate; and
mixing the oxidant first part with the reductant second part to form a mixed composition, wherein the mixed composition has a pH from 8.5 to 11.0; and
contacting the mixed composition with a surface to provide oxidizing benefits to the surface whereby the oxidant is reduced by the reductant to prevent damage caused by prolonged exposure to the hypohalous acid or the hypohalite.

12. The method of claim 11, further comprising a pH buffer comprising at least one of an organic acid, a phosphate, a bicarbonate or a carbonate.

13. The method of claim 12, wherein the buffer is carbonate.

14. The method of claim 12, wherein the second part comprises the buffer.

15. The method of claim 11, wherein the oxidant is hypochlorite.

16. The method of claim 11, wherein the surface is a hard surface.

17. The method of claim 11, wherein the surface is a soft surface.

* * * * *